United States Patent [19]
Biller et al.

[11] Patent Number: 5,428,028
[45] Date of Patent: Jun. 27, 1995

[54] METHOD FOR LOWERING CHOLESTEROL EMPLOYING A PHOSPHONOMETHYLPHOSPHINATE SQUALENE SYNTHETASE INHIBITOR

[75] Inventors: Scott A. Biller, Ewing; David R. Magnin, Hamilton, both of N.J.

[73] Assignee: E. R. Squibb & Sons, Inc., Princeton, N.J.

[21] Appl. No.: 897,119

[22] Filed: Jun. 11, 1992

Related U.S. Application Data

[63] Continuation of Ser. No. 699,408, May 13, 1991, abandoned.

[51] Int. Cl.⁶ ............................................. A61K 31/66
[52] U.S. Cl. ................................... 514/102; 514/107; 514/108
[58] Field of Search ...................... 514/102, 107, 108

[56] References Cited

U.S. PATENT DOCUMENTS

| | | | |
|---|---|---|---|
| 4,371,527 | 2/1983 | Bentzen | 514/107 |
| 4,871,721 | 10/1989 | Biller | 514/102 |
| 4,924,024 | 5/1990 | Biller | 558/202 |
| 5,157,027 | 10/1992 | Biller | 514/107 |

FOREIGN PATENT DOCUMENTS

| | | | |
|---|---|---|---|
| 0298553A1 | 1/1989 | European Pat. Off. | |
| 0298553 | 1/1989 | European Pat. Off. | C07F 9/38 |
| 0356866A2 | 3/1990 | European Pat. Off. | |
| 0409181A3 | 1/1991 | European Pat. Off. | |

OTHER PUBLICATIONS

Kramsch et al. Science 213;1511–1512 Sep. 25, 1981.

*Primary Examiner*—Marianne M. Cintins
*Assistant Examiner*—Kimberly R. Jordan
*Attorney, Agent, or Firm*—Burton Rodney

[57] ABSTRACT

A method is provided for inhibiting cholesterol biosynthesis by inhibiting de novo squalene production employing methylene phosphonoalkylphosphinate compounds.

22 Claims, No Drawings

5,428,028

METHOD FOR LOWERING CHOLESTEROL EMPLOYING A PHOSPHONOMETHYLPHOSPHINATE SQUALENE SYNTHETASE INHIBITOR

This is a continuation of application Ser. No. 699,408, filed May 13, 1991, now abandoned.

FIELD OF THE INVENTION

The present invention relates to a method for inhibiting cholesterol biosynthesis by inhibiting de novo squalene production employing a phosphonomethylphosphinate squalene synthetase inhibitor.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413–441, J. Wiley and Sons, 1981 and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase, along with HMG-CoA reductase has been shown to be down-regulated by receptor mediated LDL uptake (Faust, J. R.; Goldstein, J. L.; Brown, M. S. *Proc. Nat. Acad. Sci. USA*, 1979, 76, 5018–5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

DESCRIPTION OF THE INVENTION

In accordance with the present invention, a method is provided for inhibiting the enzyme squalene synthetase to thereby inhibit cholesterol biosynthesis so as to enable inhibiting or treating hypercholesterolemia, wherein a methylene phosphonoalkylphosphinate ester also referred to as a phosphonomethylphosphinate and/or salt thereof as described in European Patent Application 0298553A1 (Norwich Eaton Pharmaceuticals, Inc.), published Jan. 11, 1989, (hereinafter referred to as EP 0298553) is employed.

The EP 0298553 compounds useful in the method of the invention are methylene phosphonoalkylphosphinic acids, and the pharmaceutically acceptable salts and esters thereof, having the general structure:

(1)

wherein

R₁ is selected from hydrogen, substituted alkyl and unsubstituted alkyl.

A and B are independent substituent moieties, at least one of which is a lipophilic group.

The term "lipophilic group" refers to a group which contains at least six carbons (preferably greater than 10) and preferably less than 2 polar substituents bearing OH, NH or C=O functions. The lipophilic substituent is required for strong enzyme inhibitor binding and inhibition of the enzyme squalene synthetase or other enzymes in the cholesterol biosynthetic pathway such as in the pathway from isopentenyl diphosphate to squalene, that is, farnesyl diphosphate synthetase and isopentenyl diphosphate - dimethylallyl diphosphate isomerase.

The term "alkyl" as used herein, unless otherwise specified, means chemically-stable carbon-containing chains which may be straight, branched, or cyclic; and further which may be saturated, monounsaturated (e.g., one double bond; one triple bond), or polyunsaturated (e.g. two double bonds; two triple bonds; three double bonds; one double and one triple bond). Preferred alkyl have from 1 to about 20 carbon atoms. "Cycloalkyls" as used herein, having from about 3 to about 10 carbon atoms are preferred. Also preferred are straight chain alkyl, saturated alkyl or monounsaturated alkyl.

Alkyl is preferably unsubstituted but may be substituted. Preferred substituent groups for alkyl are as follows: halogen, nitro, cyano, heterocycle, aryl, heteroaryl, unsubstituted amino, and the amide thereof derived from a carboxylic acid of an alkyl, heterocycle, aryl or heteroaryl group, amino substituted with one alkyl, heterocycle, aryl or heteroaryl group and the amide thereof derived from a carboxylic acid of an alkyl group, amino substituted independently with one alkyl group and one alkyl, heterocycle, aryl or heteroaryl group, hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof, —SO₃H, the pharmaceutically acceptable salts therof, the ester thereof derived from an alcohol of an alkyl group, the unsubstituted amide thereof, and the amide thereof substituted with one or two alkyl groups, —CO₂H, the pharmaceutically acceptable salts thereof, the ester thereof derived from an alcohol of an alkyl group, the unsubstituted amide thereof, and the amide thereof substituted with one or two alkyl groups, PO₃H₂, the pharmaceutically acceptable salts thereof, the ester thereof derived from an alcohol of an alkyl group, the unsubstituted amide thereof, and the amide thereof substituted with one or two alkyl groups, —(R⁸)PO₂H (where R⁸ is hydrogen or unsubstituted lower alkyl), the pharmaceutically acceptable salts thereof, the ester thereof derived from an alcohol of an alkyl group, the unsubstituted amide thereof, and the amide thereof substituted with one or two alkyl groups, aldehyde, ketone having an alkyl group, carbamate, unsubstituted or substituted with one or two alkyl groups, peptidyl, and combinations thereof.

The term "lower alkyl" as used herein, unless otherwise specified, means unsubstituted alkyl having from 1 to about 6 carbon atoms which may be saturated or unsaturated. Preferred lower alkyl are saturated and have from one to about 4 carbon atoms. For lower alkyl groups specified herein as substituted, preferred substituents are the same as for alkyl hereinabove.

The term "heterocycle" as used herein, unless otherwise specified, means chemically-stable non-aromatic rings, including fused non-aromatic rings, having from about 5 to about 20 atoms, comprising at least one heteroatom selected from nitrogen, sulfur, phosphorus and oxygen. Preferred are 5 and 6 membered ring heterocycles which comprise from about 1 to about 3 heteroatoms. More preferred are 5 and 6 membered ring heterocycles which comprise one or two heteroatoms (especially nitrogen heteroatoms). Most preferred are the 6 membered ring heterocycles comprising one nitrogen atom, especially piperidinyl and piperidinylidene heterocycles. Heterocycles may be unsubstituted or substituted, saturated or unsaturated. Preferred heterocycles are unsubstituted or substituted with alkyl; halogen; nitro; cyano; heterocycle; aryl; heteroaryl; unsubstituted amino, and the amide thereof derived from a carboxylic acid of an alkyl heterocycle, aryl or heteroaryl group; amino substituted with one alkyl, heterocycle, aryl or heteroaryl group and the amide thereof derived from a carboxylic acid of an alkyl group; amino substituted independently with one alkyl group and one alkyl, heterocycle, aryl or heteroaryl group; hydroxy, and the ester thereof derived from a carboxylic acid of an alkyl, heterocycle, aryl or heteroaryl group; ether having an alkyl, heterocycle, aryl or heteroaryl group; thio, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof; —$SO_3H$, the pharmaceutically acceptable salts thereof, the ester thereof derived from an alcohol of an alkyl group, the unsubstituted amide thereof, and the amide thereof substituted with one or two alkyl groups; —$CO_2H$, the pharmaceutically acceptable salts thereof, the ester thereof derived from an alcohol of an alkyl group, the unsubstituted amide thereof, and the amide thereof substituted with one or two alkyl groups; $PO_3H_2$, the pharmaceutically acceptable salts thereof, the ester thereof derived from an alcohol of an alkyl group, the unsubstituted amide thereof, and the amide thereof substituted with one or two alkyl groups; —($R^8$)$PO_2H$ (where $R^8$ is hydrogen or unsubstituted lower alkyl), the pharmaceutically acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; peptidyl, and combinations thereof.

The term "aryl", as used herein, unless otherwise specified, mean chemically-stable aromatic rings, including fused aromatic rings, having from about 6 to about 20 carbon atoms. Preferred aryl are phenyl or naphthyl, most preferred is phenyl. Aryls may be unsubstituted or substituted. Preferred aryls are unsubstituted or substituted with alkyl; halogen; nitro; cyano; heterocycle; aryl; heteroaryl, unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a caroxylic acid of an alkyl group; amino substituted independently with one alkyl group and one alkyl, heterocycle, aryl or heteroaryl group; hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof; —$SO_3H$, the pharmaceutically acceptable salts thereof, the ester thereof derived from an alcohol of an alkyl group, the unsubstituted amide thereof, and the amide thereof substituted with one or two alkyl groups; —$CO_2H$, the pharmaceutically acceptable salts thereof, the ester thereof derived from an alcohol of an alkyl group, the unsubstituted amide thereof, and the amide thereof substituted with one or two alkyl groups; $PO_3H_2$, the pharmaceutically acceptable salts thereof, the ester thereof derived from an alcohol of an alkyl group, the unsubstituted amide thereof, and the amide thereof substituted with one or two alkyl groups; —($R^8$)$PO_2H$ (where $R^8$ is hydrogen or unsubstituted lower alkyl), the pharmaceutically acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; peptidyl; and combinations thereof.

The term "heteroaryl", as used herein, unless otherwise specified, means chemically-stable aromatic rings, including fused aromatic rings and fused aromatic and non-aromatic rings, having from about 5 to about 20 atoms, comprising at least one heteroatom selected from nitrogen, sulfur, phosphorus and oxygen. Preferred are 5 and 6 membered ring heteroaryls which comprise from about 1 to about 3 heteroatoms. More preferred are 5 and 6 membered ring heteroaryls which comprise one or two heteroatoms (especially nitrogen heteroatoms). Most preferred heteroaryl is pyridinyl. Heteroaryls may be unsubstituted or substituted. Preferred heteroaryls are unsubstituted or substituted with alkyl; halogen; nitro; cyano; heterocycle; aryl; heteroaryl; unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; amino substituted independently with one alkyl group and one alkyl heterocyle, aryl or heteroaryl group; hydroxy, and the ester thereof derived from a carboxylic acid of an alkyl heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide and sulfone derivatives thereof; —$SO_3H$, the pharmaceutically acceptable salts thereof, the ester thereof derived from an alcohol of an alkyl group, the unsubstituted amide thereof, and the amide thereof substituted with one or two alkyl groups; —$CO_2H$, the pharmaceutically acceptable salts thereof, the ester thereof derived from an alcohol or an alkyl group, the unsubstituted amide thereof, and the amide thereof substituted with one or two alkyl groups; $PO_3H_2$, the pharmaceutically acceptable salts thereof, the ester thereof derived from an alcohol of an alkyl group, the unsubstituted amide thereof, and the amide thereof substituted with one or two alkyl groups; —($R^8$)$PO_2H$ (where $R^8$ is hydrogen or unsubstituted lower alkyl), the pharmaceutically acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; peptidyl; and combinations thereof.

The term "substituent group", as used herein, means hydrogen or an alkyl, heterocycle, aryl or heteroaryl group, unless otherwise specified.

$R_1$ is a moiety selected from hydrogen, and alkyl. Preferred $R_1$ is unsubstituted alkyl, especially lower alkyl. Preferred substituents on the $R_1$ alkyl, when substituted, include halogen, alkoxy, unsubstituted and substituted phenyl, hydroxy, carboxy, and chemically-stable combinations thereof.

A is a moiety selected from the group consisting of hydrogen; halogen; nitro; alkyl; heterocycle; aryl; heteroaryl; unsubstituted amino, and the amide thereof derived from a carboxylic acid of a substituent group; amino substituted with one substituent group, and the amide thereof derived from a carboxylic acid of a substituent group; amino substituted independently with one alkyl group and one substituent group; hydroxy, and the ester thereof derived from a carboxylic acid of a substituent group; ether having a substituent group; thiol, and the thiol ester thereof derived from a carboxylic acid of a substituent group; thioether having a substituent group, and the sulfoxide and sulfone derivative thereof; —$SO_3H$, the pharmaceutically acceptable salts thereof, the ester thereof derived from an alcohol of a substituent group, the unsubstituted amide thereof, and the amide thereof substituted with one or two alkyl groups; —$CO_2H$, the pharmaceutically acceptable salts thereof, the ester thereof derived from an alcohol of a substitutent group, the unsubstituted amide thereof, and the amide thereof substituted with one or two alkyl groups; aldehyde; ketone having a substituent group; carbamate, unsubstituted or substituted with one or two alkyl groups; pepetides having from about one to about 100 amino acid moieties; or the A and B moieties are covalently linked to form a ring having from 3 to about 7 atoms with from 0 to about 3 heteroatoms selected from the group consisting of nitrogen, sulfur, phosphorus and oxygen, the ring being unsubstituted or substituted with one or more of the above substituents of A; or the A and B moieties are replaced by an unsubstituted or substituted alkyl moiety attached to the geminal carbon by a double bond.

Examples of A moieties include
(1) hydrogen;
(2) halogen; more preferred are F or Cl;
(3) substituted and unsubstituted alkyl having the general structure:

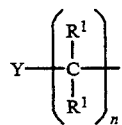

(2)

wherein
n is an integer from 1 to about 10, preferably from 1 to about 5, more preferably n=1 or 2, and most preferably n=1;
each $R^1$ is independently selected to achieve chemically-stable moieties from the group consisting of hydrogen, halogen, lower alkyl, unsubstituted amino or the amido thereof derived from a carboxylic acid of a lower alkyl group, amino substituted with one lower alkyl group or the amide thereof derived from a carboxylic acid of a lower alkyl group, amino substituted independently with two lower alkyl groups, hydroxy or the ester thereof derived from a carboxylic acid of a lower alkyl group, —$CO_2H$ or the pharmaceutically acceptable salts thereof or the ester thereof derived from an alcohol of a lower alkyl group or the unsubstituted amide thereof or the amide thereof substituted with one or two lower alkyl groups, ether having a lower alkyl group, —$PO_3H_2$ or the pharmaceutically acceptable salts thereof, and nitro, or two $R^1$'s on the same carbon atom are =O or =$NR^9$ (where $R^9$ is lower alkyl or may be hydrogen when there is another nitrogen atom attached to the same carbon atom as the =$NR^9$ moiety), or two $R^1$'s on adjacent carbon atoms may be replaced by an additional bond between the carbon atoms; or an $R^1$ on the first carbon atom (from the right side of structure (2) hereinabove) and B (see structure (1) hereinabove) may be replaced by an additional bond; and Y is a substituent of alkyl as defined hereinbefore; (for the sake of chemical stability of the compounds used in the present invention, $R^1$ cannot be such that there is a halogen and an oxygen or sulfur or nitrogen singly bonded to the same carbon atom or such that two of an oxygen or sulfur or nitrogen are singly bonded to the same carbon atom);

(4) Cycloalkyl having from about 4 to about 10 carbon atoms; more preferred are cycloalkyl having 5 or 6 carbon atoms;

(5) Heterocycle having 5 or 6 atoms in the ring; more preferred are heterocycles having one or two nitrogen atoms in the ring, more preferred still are heterocycles having one nitrogen atom in the ring; most preferred are unsubstituted or substituted piperidinyl, pyrrolidinyl, piperazinyl, morpholinyl;

(6) unsubstituted and substituted phenyl; naphthyl;

(7) Unsubstituted and substituted 5 and 6 membered ring heteroaryls having one or two heteroatoms (especially nitrogen heteroatoms); most preferred is pyridinyl;

(8) amine-containing moiety having the general structure:

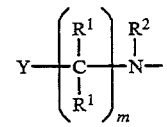

wherein
m is an integer from 0 to about 10, preferably from 0 to about 5, more preferably 0 or 1, and most preferably m=0;
$R^1$ and Y are as described hereinbefore; and
$R^2$ is hydrogen, lower alkyl or acyl derived from a carboxylic acid of a lower alkyl;

(9) oxygen-containing moiety having the general structure:

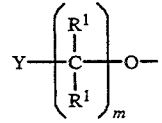

wherein
  m is an integer from 0 to about 10, preferably from 0 to about 5, more preferably 0 or 1, and most preferably m=0; and
  $R^1$ and Y are as described hereinbefore; and
(10) sulfur-containing moiety having the general strucutre:

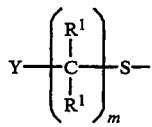

wherein
  m is an integer from 0 to about 10, preferably from 0 to about 5, more preferably 0 or 1, and most preferably m=0; and
  $R^1$ and Y are as described hereinbefore;
(11) peptide-containing moiety having the general structure:

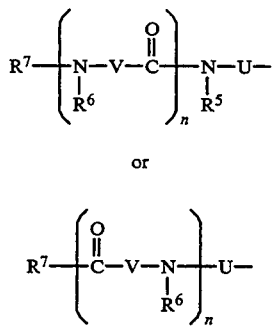

wherein
  n is an integer from 1 to about 100, preferably from 1 to about 6;
  $R^5$ each $R^6$ and $R^7$ are independently hydrogen or lower alkyl, preferably $R^5$, each $R^6$ and $R^7$ are hydrogen;
  U and each V are independently unsubstituted or substituted lower alkyl (substituted such that moiety is chemically-stable), or $R^5$ and U or each $R^6$ and V, together with the included nitrogen atom to which they are bound, may form a five- or six-membered ring which is unsubstituted or substituted; or U may be nil; preferably U and each V or rings in which they are incorporated are moieties found in naturally-occurring amino acid moieties, i.e., lysine, leucine, isoleucine, valine, phenylalanine, arginine, histidine, methionine, alanine, aspartic acid, threonine, proline, glycine, serine, tyrosine, tryptophan, glutamine and cysteine.

Preferred A moieties of the present invention are optionally substituted alkyl, optionally substituted alkenyl, and optionally substituted aryl.

B is a moiety selected from hydrogen; halogen; unsubstituted and substituted lower alkyl; unsubstituted and substituted cycloalkyl having from about 3 to about 7 atoms in the ring; unsubstituted and substituted heterocycle having from about 3 to about 7 atoms in the ring; unsubstituted and substituted phenyl; hydroxy, and the ester thereof derived from a carboxylic acid of a lower alkyl group; thiol; unsubstituted amino, and the amide thereof derived from a carboxylic acid of a lower alkyl group; amino substituted with one lower alkyl group, and the amide thereof derived from a carboxylic acid of a lower alkyl group; amino substituted independently with two lower alkyl groups; $-CO_2H$, the pharmaceutically acceptable salts thereof, the ester thereof derived from an alcohol of a lower alkyl group, the unsubstituted amide thereof, and the amide thereof substituted with one or two lower alkyl groups.

For the sake of chemical stability for the compounds of the present invention, it is preferred that the A and B moieties do not both have heteroatoms (N, O or S), or a heteroatom and a halogen, bonded to the methylene phosphonoalkylphosphinate moiety (i.e., the carbon atom geminally substituted with the phosphorus atoms). Thus, when the A moiety has an oxygen, sulfur, nitrogen, or halogen atom bonded to the phosphorus-substituted methylene carbon, then B is selected from hydrogen; unsubstituted or substituted lower alkyl, cycloalkyl, heterocycle (where a carbon atom of the heterocycle is bonded to the geminal carbon atoms), or phenyl; $-CO_2H$, the pharmaceutically acceptable salts thereof, the ester thereof derived from an alcohol of a lower alkyl group, the unsubstituted amide thereof, and the amide thereof substituted with one or two lower alkyl groups.

Preferred B is selected from hydrogen, halogen, unsubstituted and substituted lower alkyl, unsubstituted and substituted phenyl, unsubstituted and substituted benzyl, hydroxy and the ester thereof derived from a carboxylic acid of a lower alkyl group, thiol, unsubstituted amino and the amide thereof derived from a carboxylic acid of a lower alkyl group, amino substituted with one lower alkyl group and the amide thereof derived from a carboxylic acid of a lower alkyl group, amino substituted independently with two lower alkyl groups, and $-CO_2H$, and the pharmaceutically acceptable salts thereof and the ester thereof derived from an alcohol of a lower alkyl group and the unsubstituted amide thereof or the amide thereof substituted with one or two lower alkyl groups.

The method of the invention is carried out employing methylene phosphonoalkylphosphinate compounds which inhibit cholesterol biosynthesis by inhibition of de novo squalene production. These methylene phosphonoalkylphosphinate compounds (which are described in detail hereinbefore) inhibit the squalene synthetase enzyme and, in addition, some of these compounds inhibit other enzymes in the pathway from isopentenyl diphosphate to squalene, that is, farnesyl diphosphate synthetase and isopentenyl diphosphate-dimethylallyl diphosphate isomerase.

Thus, the method of the invention is useful in treating atherosclerosis to inhibit progression of disease and in treating hyperlipidemia to inhibit development of atherosclerosis. In addition, the method of the invention may be employed to increase plasma high density lipoprotein cholesterol levels.

The method of the invention may also be carried out employing the methylene phosphonoalkylphosphinate squalene synthetase inhibitor in combination with an antihyperlipoproteinemic agent such as probucol and/or with one or more serum cholesterol lowering agents such as Lopid (gemfibrozil), fibric acid derivatives such as bezafibrate, bile acid sequestrants such as cholestyramine, colestipol, polidexide (DEAE-Sephadex) as well as clofibrate, nicotinic acid and its derivatives, neomycin, p-aminosalicyclic acid, bezafibrate and the like and/or one or more HMG CoA reductase inhibitors such as lovastatin, pravastatin, velostatin or simvastatin.

The above compounds to be employed in combination with the squalene synthetase inhibitor of the invention will be used in amounts as indicated in the Physicians' Desk Reference (PDR).

The compounds employed in the methods of the invention may also be employed with sodium lauryl sulfate or other pharmaceutically acceptable detergents to enhance oral bioavailability of such compounds.

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985).

Preparation of Rat Liver Microsomes

Livers are dissected from 2 or 3 decapitated Sprague Dawley rats and are quickly transferred to ice cold buffer (potassium phosphate, 0.05M, (pH 7.4); $MgCl_2$, 0.004M; EDTA, 0.001M; and 2-mercaptoethanol 0.01M) and rinsed thoroughly. The livers are minced in cold buffer (2.0 ml/g) and homogenized using a Potter-Elvejhem homogenizer. The homogenate is centrifuged at 5,000 x g, 10 minutes (4° C.), and the supernatant poured through layers of cheese cloth. The supernatant is then centrifuged at 15,000 x g for 15 minutes (4°). Again the supernatant is filtered through 2 layers of cheese cloth, and centrifuged a third time at 100,000 x g for 1.0 hour at 4° C. Following centrifugation the microsomal pellet is resuspended in a volume of buffer equivalent to 1/5 the volume of the original homogenate, and homogenized in a ground glass homogenizer. Aliquotted microsomes are frozen at −80° C., and retain activity for at least two months.

Enzyme Assay

Reaction Mixtures are prepared in 50 ml round bottom pyrex glass tubes with tight-fitting, teflon-lined, screw caps. Tubes are cooled to 4° C., and the following components are added in sequence:

| 1. Potassium phosphate buffer (0.275 M, pH 7.4) | 0.36 ml |
|---|---|
| 2. KF (55 mM) | 0.36 ml |
| 3. NADPH (5.0 mM, freshly prepared) | 0.36 ml |
| 4. $H_2O$ (or $H_2O$ + test compound) | 0.16 ml |
| 5. $MgCl_2$ (27.5 mM) | 0.36 ml |
| 6. Microsomal Enzyme (0.48 mg microsomal protein in homogenization buffer) (15 µl prep.) 4/23/86 | 0.20 ml |
| | 1.8 ml |

This mixture is equilibrated under $N_2$ at 4° C. for 5–15 minutes. Reaction mixtures are then warmed to 30° C., and the enzyme reaction initiated by adding 0.2 ml of farnesyl pyrophosphate (219 µM) prepared in $H_2O$. Each tube is again overlayered with $N_2$, and incubated at 30° C. for 60 minutes. The reaction is stopped by the addition of 1.0 ml KOH (40%). Ethanol (95%) (spectral grade) (1.0 ml) is added to each tube. Docasane (5 nmoles in hexane) is added to each tube as an internal standard. The mixture is saponified at 65° C. for 30 minutes. The tubes are cooled to room temperature and extracted twice with 10.0 ml spectral grade hexane.

The upper organic phase fractions are pooled in glass 20.0 ml scintillation vials and reduced in volume to ≈1.0 ml under a stream of $N_2$. The sample is then transferred to acid-washed, conical bottom, glass (1.0 ml) microvials, and brought to dryness under $N_2$. The residue is resuspended in 50 µl hexane (spectral grade), and these samples are spun at 1000 rpm at room temperature for 10 minutes. Following centrifugation approximately 40 µl of supernatant is transferred to 100 µl acid-washed microvials with septa/crimp-top caps (compatible with the Hewlett-Packard GC auto injector).

Gas Chromatagraphy

Two µL of each sample is injected onto a fused silica megabore DB-17 column (15M×0.525 mm) (J&W Scientific) using a splitless mode of injection. Gas flow rates are listed below:

| Make up gas (helium) | 20 ml/min. |
|---|---|
| Air | 400 ml/min. |
| Hydrogen | 30 ml/min. |
| Carrier (helium) | 15 ml/min. |
| Septum purge vent | 5 ml/min. |
| | (Septum purge off 0.00 min., on at 0.5 min.) |

The injector temperature is 200° C., and the FID detector temperature is set at 270° C. Oven temperature is programmed through a two ramp sequence as follows:

Oven:
Initial temperature 180° C., initial time 10 minutes
Ramp one: 20° C./minute
Second temperature 250° C., second time 10 minutes
Ramp two: 20° C./minute
Third temperature 260° C., third time 10 minutes
(Equilibration time 1.0 minute)

Using this gas chromatographic system, docasane (internal standard) has a retention time of 3.6–3.7 minutes, and squalene has a retention time of 14.7–14.9 minutes. The amount of squalene in each reaction mixture is determined by obtaining the areas under the squalene and docasane peaks and using the following formula to calculate the amount of squalene (nmoles) in the total reaction mixture.

Squalene (nmoles/reaction mixture) =

5.0 (nmoles docasane × internal standard)

$$\frac{(\text{Squalene Peak Area})}{\text{Docasane Peak Area}} \times RR^*$$

*RR = Response Ratio [Docasane/Squalene]
*RR = 0.56

Compounds Testing

Compounds are dissolved in $H_2O$ and added to reaction mixtures prior to addition of farnesyl pyrophosphate substrate. All reaction mixtures are run in duplicate, at several concentrations. Additionally, all compound $I_{50}$ values are derived from composite dose response data.

In carrying out the method of the invention, a pharmaceutical composition will be employed containing at least one methylene phosphonoalkylphosphinate squalene synthetase inhibitor in association with a pharmaceutical vehicle or diluent. The pharmaceutical compostion can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains methylene phosphonoalkylphosphinate squalene synthetase inhibitor (250 mg), lactose (75 mg) and magnesium stearate (15 mg). The mixture is passed through a 60 mesh sieve and packed into a No. 1 gelatin capsule.

A typical injectible preparation is produced by asceptically placing 250 mg of sterile methylenephosphonoalkylphosphinate squalene synthetase inhibitor into a vial, asceptically freeze-drying and sealing. For use, the contents of the vial are mixed with 2 ml of physiological saline, to produce an injectible preparation.

The following Examples illustrate the preparation of preferred methylene phosphonoalkylphosphinate compounds which may be employed in the method of the invention for inhibiting cholesterol biosynthesis by inhibiting de novo squalene production.

Introduction to Experimental

All temperatures are reported in degrees Centigrade.

$^1$H and $^{13}$C chemical shifts are reported as δ-values with respect to Me$_4$Si (δ=0). $^{31}$P spectra were measured on a JEOL FX90Q FT-NMR spectrometer, at 36.2 MHz, utilizing the $^1$H decoupled mode. The $^{31}$P data were obtained using 85% H$_3$PO$_4$ as an external reference (δ=0). Coupling constants J are reported in Hz. Chemical ionization mass spectra (CI-MS) were determined with a Finnigan TSQ-4600 instrument equipped with a direct exposure probe using the indicated reagent gases. Fast atom bombardment mass spectra (FAB-MS) were recorded on a VG Analytical ZAB-2F spectrometer. Ions were sputtered (8keV Xe) from a matrix containing dithiothreitol, dithioerythritol, DMSO, glycerol and water.

All reactions were carried out under an atmosphere of dry argon or nitrogen. The following reagents and solvents were distilled prior to use from the indicated drying agents, where applicable: CH$_2$Cl$_2$, 2,4,6-collidine, and diisopropylamine (CaH$_2$); THF and diethyl ether (K, benzophenone); N,N-diethyltrimethylsilylamine and oxalyl chloride. Benzene was passed through neutral alumina (activity I) and stored over 4A-molecular sieves. Lithium bromide was dried at 100° C. over P$_2$O$_5$.(E,E)-Farnesol was purchased from Aldrich Chemical Company.

TLC was performed on E. Merck Silica Gel 60 F-254 plates (0.25 mm) or E. Merck Cellulose F plates (0.1 mm). Flash chromatography was carried out using E. Merck Kieselgel 60 (230–400 mesh).

Reverse-phase chromatographic purification of salts or mixed ester-salts was carried on CHP20P gel or SP207SS gel, a highly porous, polystyrenedivinyl benzene copolymer available from Mitsubishi Chemical Industries. The indicated general procedure was followed: An FMI Model RP-SY pump was utilized for solvent delivery. A column of CHP20P or SP207SS (2.5 cm diameter, 12–22 cm height) was slurry packed and washed with water (500–1000 mL), and a basic, aqueous solution of the crude salt was applied to the top of the column. Typically, the column was eluted with water, followed by a gradient composed of increasing concentrations of acetonitrile or methanol in water. The gradient was created by placing the tip of a tightly stoppered separatory funnel containing 300–500 mL of the organic solvent, or an aqueous-organic mixture, just beneath the surface of a reservoir containing 300–500 mL of pure water. To start the gradient, the stopcock of the separatory funnel was opened, so that as the solvent was withdrawn by the pump from the reservoir, it was replaced with the solvent from the separatory funnel. HPLC-grade solvents and Lectrostill steam distilled water were employed. Fractions were collected (10–15 mL each) at a flow rate of 5–10 mL per minute. Those fractions that contained pure product as judged by TLC were pooled, the organic solvents were evaporated and the aqueous residue was lyophilized to dryness.

The following abbreviations as used in the working Examples.

Me=methyl
Et=ethyl
Bu=n-butyl
OAc=acetate

EXAMPLE 1

(E,E)-[1-(Hydroxymethylphosphinyl)-7,11,15-trimethyl-6,10,14-hexadecatrienyl]phosphonic acid, disodium salt A. (Ethoxymethylphosphinyl)methyl]phosphonic acid, diethyl ester Diethyl methylphosphonite 10.0 g (73.5 mmol) was heated (130° C. bath temperature) with 14.9 g (80.0 mmol) of diethylchloromethylphosphonate for 48 hours under argon. At this point the contents of the reaction were fractionally distilled to provide 11.0 g (56%) of title compound (bp 125° C./0.8 mm Hg) as a colorless liquid.

$^1$H NMR (CDCl$_3$, 270 MHz): δ 4.0 (m, 6H), 2.3 (dd, 2H, J=21.1, 17.6 Hz), 1.6 (d, 3H, J=14.6 Hz), 1.2 (t, 9H, J=7.0 Hz) ppm.

B. (E,E)-6,10,14-Trimethyl-5,9,13-pentadecatrien-1-yl iodide (1) (E,E)-1-Chloro-3,7,11-trimethyl-2,6,10-dodecatriene (Note: all temperatures indicated are for the contents of the reaction flask). To a stirred solution of 299 mg (2.24 mmol) of N-chlorosuccinimide in 15 mL of dichloromethane at −30° C. under argon was added 0.18 mL (2.45 mmol) of distilled dimethyl sulfide over 5 minutes. After 10 minutes at −30° C., the reaction was allowed to warm to 0° C. for 10 minutes, followed by cooling to −40° C. A solution of 441.4 mg (1.99 mmol) of 3,7,11-trimethyl-2,6,10-tridecatrien-1-ol in 5 mL of dichloromethane was added dropwise over 10 minutes. The reaction was allowed to warm gradually to 0° C. over 1 hour, and then maintained for 1 hour. After quenching with cold water, the mixture was extracted with hexane and the hexane extract was washed with cold water and cold brine, dried (MgSO$_4$) and evaporated to afford 483 mg of a crude product. Rapid flash chromatography on 20 g of silica gel eluted with 3:97 ethyl acetate:petroleum ether provided 406.5 mg (85%) of a colorless liquid. $^{13}$C NMR indicated that this material contained a trace (3%) impurity.

TLC: Silica gel (2:98 ethyl acetate:hexane) $R_f$=0.56.

$^1$H NMR (CDCl$_3$, 270 MHz): δ 5.44 (t, 1, J=7.9 Hz), 5.09 (t, 2, J=5.8 Hz), 4.07 (d, 2, J=7.9 Hz), 1.9–2.2 (m, 9), 1.72 (s, 3), 1.68 (s, 3), 1.60 (s, 6) ppm.

(2) Dichloro[mu-[1-propanolato(2-)C$^3$:O$^1$]]dimagnesium

A modification of the procedure of G. Cahiez et al was employed (Tetrahedron Letters, 1978, 3013–4): To a stirred solution of 28.55 g (301.9 mmol) of 3-chloro-1-propanol in 300 mL of THF under argon at −20° C. was added 101 mL (303 mmol) of 3M methylmagnesium chloride in THF over 20 minutes. After 30 minutes at −20° C., the reaction was allowed to warm to room temperature, 11 g (452.8 mmol) of magnesium turnings were added and the reaction was heated to reflux. At the start of reflux, 0.60 mL (6.94 mmol) of 1,2-dibromoethane were added, and after 1 hour at reflux another 0.60 mL was added. After refluxing for a total of 2 hours, the reaction was allowed to cool to room temperature.

(3). (E,E)-6,10,14-Trimethyl-5,9,13-pentadecatrien-1-ol

A solution of 37.5 mL (20.3 mmol, 5.1 eq.) of a 0.54M solution of Grignard reagent (Part (2)) in tetrahydrofuran and 9 mL of hexamethylphosphoramide at room temperature under argon was treated over 10 minutes with a solution of 955.5 mg (3.97 mmol) of (E,E)-farnesyl chloride (Part (1)) in 5 mL of tetrahydrofuran. After one hour, the reaction mixture was diluted with a mixture of 1:1 diethyl ether:hexane and quenched with 1M HCl. The organic phase was washed with three 25 mL portions of saturated NaHCO$_3$, three 25 mL portions of H$_2$O, and 25 mL of brine, dried over MgSO$_4$ and evaporated to obtain 995.0 mg of crude product. Purification required two chromatographies. The first was run on 70 g of silica gel, eluting with 1:99 ethyl acetate:CH$_2$Cl$_2$ to provide 484.3 mg of impure material and 307.7 mg of pure title compound. The second chromatography, of the impure fractions, on 50 g of silica gel eluted with 0.75:99.25 ethyl acetate: CH$_2$Cl$_2$ gave 117.2 mg of slightly impure material and 302.8 mg of pure title compound. Combination of pure material from both columns gave a yield of 610.5 mg (58%) of pure desired title isomer.

TLC: Silica gel (10:90 ethyl ether:CH$_2$Cl$_2$) $R_f$=0.38.

IR (CCl$_4$)3639, 3450, 2964, 2930, 2858, 1449, 1382, 1058, 1028, 776, 750 cm$^{-1}$.

$^1$H NMR (CDCl$_3$, 270 MHz): δ 5.10 (m, 3H), 3.62 (t, 2H, J=6.5 Hz ), 2.00 (m, 10H ), 1.69 (s, 3H ), 1.61 (s, 9H), 1.2–1.7 (m, 5H, OH) ppm.

Mass Spec (CI-CH$_4$/N$_2$O, +ions) m/e 282 (M+NH$_4$), 265 (M+H), 263 (M+H−H$_2$).

(4) (E,E)-6,10,14-Trimethyl-5,9,13-pentadecatrien-1-yl iodide

To a stirred solution of 363.8 mg (1.38 mmol) of Part (3) alcohol in 6 mL of dichloromethane at 0° C. was added 0.39 mL (2.76 mmol) of triethylamine followed by the dropwise addition of 0.14 mL (2.76 mmol) of methanesulfonyl chloride over 5 minutes. After stirring for 1 hour at 0° C., the mixture was diluted with ether and the organic phase was washed with 10% HCl water saturated NaHCO$_3$ and brine, dried (MgSO4) and evaporated to give 458.8 mg of the mesylate as a colorless oil.

The crude mesylate was dissolved in 10 mL of acetone, treated with 414 mg (2.76 mmol) of sodium iodide and heated to 40° C. under argon for 17 hours. The mixture was diluted with hexane, washed with water, 4% sodium thiosulfate, water and brine, dried (MgSO$_4$), evaporated to provide a colorless oil. Flash chromatography on 30 g of silica gel eluted with hexane gave 466.6 mg (90%) of the pure title iodide as a colorless oil.

TLC: Silica gel (Hexane) $R_f$=0.32.

IR (CCl$_4$) 2965, 2927, 2854, 1449, 1381, 1222, 809 cm$^{-1}$.

$^1$H NMR (CDCl$_3$, 270 MHz): δ 5.10 (m, 3H, H$_2$, H$_6$, H$_{10}$), 3.18 (t, 2H, J=7 Hz, H$_{18}$), 2.00 (m, 10H, H$_1$, H$_4$, H$_5$, H$_8$, H$_9$), 1.82 (quint, 2H, J=7 Hz, H$_{17}$), 1.68 (s, 3H, H$_{12}$), 1.60 (s, 9H, H$_{13}$, H$_{14}$, H$_{15}$), 1.44 (m, 2H, H$_{16}$) ppm.

Mass Spec (CI-CH$_4$/N$_2$O, +ions) m/e 392 (M+NH$_4$), 375 (M+H).

C. (E,E)-[1-(Ethoxymethylphosphinyl)-7,11,15-trimethyl-6,10,14-hexadecatrienyl]phosphonic acid, diethyl ester To a suspension of 134 mg (5.60 mmol) of NaH in 3 mL of dry DMF and 6 mL of dry THF at 0° C. under argon was added 1.50 g (5.60 mmol) of Part A compound over 5 minutes to give a yellow solution. The reaction was allowed to warm to room temperature and stir for 0.5 hours when 0.69 g (1.80 mmol) of Part B iodide was added in one portion. The reaction mixture was stirred for 18 hours when it was quenched with saturated aqueous NH$_4$Cl solution and diluted with ethyl acetate. The organic fraction was washed with water, brine, dried (Na$_2$SO$_4$) and evaporated to provide a crude yellow oil. Flash chromatography was performed on 75 g of silica gel packed and loaded with ethyl acetate. Elution with 150 mL of ethyl acetate followed by 700 mL of 1:9 ethanol/ethyl acetate collecting in 20 mL fractions provided 0.52 g (57%) of title compound as a pale yellow oil.

TLC Silica gel (1:9 ethanol:ethyl acetate) $R_f$=0.25.

$^1$H NMR (CDCl$_3$, 270 MHz): δ 5.10 (m, 3H), 4.10 (m, 6H), 2.20 (m, 1H), 2.10–1.90 (m, 12H), 1.60 (s, 3H), 1.59 and 1.58 (two d, 3H total, J=15.0 Hz), 1.52 (s, 9H), 1.49 (m, 2H), 1.30 (m, 2H), 1.27 (t, 9H, J=7.0 Hz) ppm.

Mass Spec. (CI-NH$_3$, +ions) m/e 505 (M+H).

D. (E,E)-[1-(Hydroxymethylphosphinyl)-7,11,15-trimethyl-6,10,14-hexadecatrienyl]phosphonic acid, disodium salt To a stirred solution of 0.70 g (1.38 mmol) of Part C compound in 7 mL of dichloromethane at room temperature was added 0.60 mL (4.16 mmol) of 2,4,6-collidine followed by 0.60 mL (5.52 mmol) of bromotrimethylsilane. The reaction was allowed to stir at room temperature for 14 hours when the solvent was evaporated and the semisolid residue pumped (~1 mm pressure) for 0.5 hours. The residue was dissolved by adding 13.8 mL of 0.5N NaOH solution (6.9 mmol) then diluting with 15 mL of water. The solution was freeze dried to provide off white solids. The solids were purified by MPLC on a column of CHP20P gel (2.5 cm diam. ×23 cm height) eluting with water (150 mL) followed by a gradient created by the gradual addition of 400 mL of acetonitrile to a reservoir of 350 mL of water. Approximately 15 mL fractions were collected. The acetonitrile was removed under reduced pressure and the aqueous solution was lyophilized to provide 0.37 g (58%) of title compound as a white lyophilate. The lyophilate was dissolved in 20 mL of water and the pH of the solution adjusted to 11. The resulting solution was repurified by MPLC on a column of CHP20P gel (2.5 cm diam. ×15 cm height) eluting with water (100 mL) followed by a gradient created by the gradual addition of 500 mL of methanol to a reservoir of 300 mL of water. Approximately 10 mL fractions were collected. The pure fractions were combined and the methanol removed under reduced pressure. The remaining aqueous solution was filtered and lyophilized to provide 190 mg (29%) of title compound as a white lyophilate. HPLC indicated that the title compound was 93% pure, the remaining 7% being a mixture of cis isomers.

IR (KBr) 3433, 2966, 2925, 2855, 1635, 1448, 1292, 1159, 1086, 970, 874 cm$^{-1}$.

$^1$H NMR (D$_2$O, 400 MHz): δ 5.18 (t, 1H, J=7.0 Hz), 5.05 (q, 2H, J=7.0 Hz), 2.05 (m, 4H), 1.95 (m, 6H), 1.70–1.40 (m, 5H), 1.57 (s, 3H), 1.52 (s, 3H), 1.50 (s, 6H), 1.25 (d, 3H, J=13.9 Hz), 1.20 (m, 2H), ppm.

Mass Spec (FAB, +ions) m/e 509 (M+Na), 487 (M+H), 465 (M−Na+2H), 443 (M−2Na+3H).

Anal. Calc'd for $C_{20}H_{36}O_5Na_2P_2$+0.50 $H_2O$: C, 50.74; H, 7.88; P, 13.08 Found: C, 50.77; H, 7.94; P, 13.42.

EXAMPLE 2

(E,E)-[1-(Hydroxymethylphosphinyl)-6,10,14-trimethyl-5,9,13-pentadecatrienyl]phosphonic acid, disodium salt A. Bishomofarnesol (1) (E,E) -3,7,11-Trimethyl-2,6,10-dodecatrienyl bromide (farnesyl bromide)

A solution of 1.00 g (4.5 mmol) of (E,E)-farnesol (Aldrich, further purified by flash chromatography) in 10 mL of distilled ether at 0° C. under argon in the dark was treated dropwise with a solution of 195 μL (2.05 mmol, 0.45 eq.) of PBr$_3$ in 2 mL of diethyl ether (ether). The resultant mixture was stirred at 0° C. for one hour, then quenched with water and separated. The organic phase was washed with 5 mL of H$_2$O, 5 mL of saturated NaHCO$_3$, and 5 mL of brine, dried over Na2SO4 and evaporated to give 1.26 g (98%) of crude bromide as a clear oil.

TLC Silica (2:8 ethyl acetate:hexane) Rf=0.69.

$^1$H NMR (CDCl$_3$, 270 MHz): δ 5.52 (t, 1H, J=8.5 Hz), 5.08 (m, 2H), 4.01 (d, 2H, J=8.5 Hz), 1.9–2.2 (m, 8H), 1.73 (s, 3H), 1.68 (s, 3H), 1.60 (s, 6H) ppm.

(2) (E,E)-5,9,13-Trimethyl-4,8,12-tetradecatrienoic acid, 1,1-dimethylethyl ester To a solution of 9.60 mL (68.5 mmol, 1.5 eq.) of diisopropylamine in 100 mL of tetrahydrofuran (THF) at −78° C. under argon was added 28.2 mL (45.0 mmol, 1.0 eq.) of 1.6M n-butyllithium in hexanes over 20 minutes. After warming to 0° C. for 15 minutes, the solution was recooled to −78° C. and 6.05 mL (45 mmol, 1.0 eq.) of t-butyl acetate was added over 20 minutes. After an additional 15 minutes, 16.0 mL (92 mmol, 2.05 eq.) of hexamethylphosphoramide (HMPA) was added, followed by a solution of 12.53 g (45.0 mmol) of Part A(1) farnesyl bromide in 100 mL of THF over 20 minutes. The reaction was stirred at −78° C. for 2.5 hours, quenched with saturated NH$_4$Cl and allowed to warm to room temperature. After diluting with 400 mL of ethyl acetate, the mixture was washed with four 100 mL portions of water, and 200 mL of brine, dried over MgSO$_4$ and evaporated to provide 12.96 g of crude product as a yellow oil. Purification by flash chromatography on 1 kg of silica gel, eluted with 1:9 ethyl acetate:petroleum ether afforded 9.39 g (65%) of title compound as a pale yellow oil.

TLC Silica gel (2:98 ethyl acetate:hexane) R$_f$=0.16.

IR(neat) 2977, 2925, 2857, 1733, 1452, 1368, 1258, 1149 cm$^{-1}$.

$^1$H NMR(CDCl$_3$, 270 MHz): δ 5.10 (m,3H), 2.25 (m, 4H), 1.9–2.1 (m, 8H), 1.68 (s, 3H), 1.62 (s, 3H), 1.59 (s, 6H ), 1.44 (s, 9H ) ppm.

Mass Spec (CI-CH$_4$/N$_2$O) (+ions) m/e 165 (M+H-C$_4$H$_8$), 247, 183, 137, 68, 57. (−ions) m/e 319 (M−H), 279, 251, 100.

(3) Bishomofarnesol

To a stirred solution of 5.00 g (15.6 mmol) of Part (2) compound in 45 mL of dry diethyl ether at 0° C. under argon was added 592 mg (15.6 mmol, 1 mol - eq.) of lithium aluminum hydride, and the resulting suspension was stirred at room temperature for 20 hours. After cooling to 0° C., the reaction was quenched by treating with 5 mL of H$_2$O, 5 mL of 15% NaOH, and 15 mL of H$_2$O and stirring the suspension for ½ hour. After adding Na$_2$SO$_4$, the slurry was filtered through Celite, washing well with diethyl ether and evaporated to obtain 3.62 g of crude product. Purification by flash chromatography on 300 g of silica gel, eluted with 1:9 ethyl acetate:petroleum ether provided 3.516 g (90%) of bishomofarnesol as a colorless liquid.

TLC Silica gel (2:8 ethyl acetate:hexane) R$_f$=0.19.

IR(neat) 3330, 2964, 2926, 2873, 2958, 1448, 1384, 1107, 1059, 401 cm$^{-1}$.

$^1$H NMR(CDCl$_3$, 270 MHz): δ 5.10 (m, 3H), 3.63 (t, 2H, J=6.5 Hz), 1.9–2.2 (m, 10H), 1.68 (s, 3H), 1.62 (2, 3H), 1.60 (s, 7H) ppm.

Mass Spec (CI-CH$_4$/N$_2$O, +ions) m/e 251 (M+H), 249 (M+H−H$_2$), 137, 123, 109, 69.

A$^1$. Bishomofarnesol (alternative preparation)

(1)  (E,E)-5,9,13-Trimethyl-4,8,12-tetradecatrienoic acid, 1,1-diethyl ester

To a suspension of 1.62 g (40.5 mmol, 3 eq.) of a 60% suspension of sodium hydride in mineral oil (washed three times with pentane) in 150 mL of tetrahydrofuran at room temperature under argon was slowly added 6.15 mL (40.5 mmol, 3 eq.) of diethyl malonate. The resulting solution was stirred for 0.5 hours, then treated with a solution of 3.83 g (13.5 mmol) of farnesyl bromide in 10 mL of tetrahydrofuran. After stirring for 6 hours, the reaction was quenched with saturated NH$_4$Cl and diluted with 300 mL of diethyl ether. The organic layer was washed with two 100 mL portions of water and 100 mL of brine, dried over MgSO$_4$ and evaporated and the bulk of the diethyl malonate removed by spinning under high vacuum to afford 4.29 g (87%) of crude title product.

TLC Silica gel (ethyl acetate:hexane 1:9) R$_f$=0.37. (TLC shows slight amount of diethyl malonate and a second by-product.)

(2)  (E,E)-5,9,13-Trimethyl-4,8,12-tetradecatrienoic acid, 1-ethylester

A mixture of 4.103 g (11.2 mmol) of Part A$^1$ (1) diester, 200 μL (11.2 mmol, 1 eq.) of water, and 950 mg (22.4 mmol, 2 eq.) of lithium chloride in 20 mL of dimethyl sulfoxide was heated at reflux (∼190° C.) for four hours. After cooling, the reaction mixture was diluted with 180 mL of a 1:1 mixture of diethyl ether:petroleum ether and washed with five 50 mL portions of water and 50 mL of brine, dried over MgSO$_4$ and evaporated to yield 3.623 g of crude product as a yellow-orange oil. Kugelrohr distillation at 180° C. (meter setting) and 0.025 mm allowed the collection of 2.100 g of a pale yellow oil, which was, however, still contaminated (by TLC). The distillation, therefore, is unnecessary and should not be performed. Flash chromatography on 180 g of silica gel, eluted with 3:97 ethyl acetate: petroleum ether provided 1.844 g (56%) of desired title product as a pale yellow oil.

TLC Silica gel (ethyl acetate:hexanes 5:95) $R_f=0.27$.

1H-NMR (CDCl$_3$, 270 MHz): δ 5.08 (br, 3H, H$_2$, H$_6$, H$_{10}$), 4.12 (q, 2H, J=6.7 Hz, OC$\underline{H}_2$), 2.31 (m, H$_1$, H$_{16}$), 1.9–2.1 (m, 8H, H$_4$, H$_5$, H$_8$, H$_9$), 1.67 (s, 3H, H$_{12}$), 1.62 (s, 3H, H$_{15}$), 1.59 (s, 6H, H$_{13}$, H$_{14}$), 1.25 (t, 3H, J=6.7 Hz, OCH$_2$C$\underline{H}_3$) ppm.

(3) Bishomofarnesol

A solution of 7.051 g (24 mmol) of Part A[1] (2) monoester in 65 mL of dry diethyl ether at 0° C. under argon was treated in portions with 915 mg (24 mmol) of lithium aluminum hydride and stirred at room temperature for three hours. After cooling to 0° C., the reaction was quenched with 7 mL of water, 7 mL of 15% NaOH, then stirred for 15 minutes. Additional 21 mL of water was added, and the reaction was stirred 0.5 hours, then dried with Na$_2$SO$_4$. The mixture was filtered through Celite, washing well with diethyl ether, and evaporated to give 5.665 g of a colorless oil. Purification by flash chromatography on silica gel eluted with 15:85 ethyl acetate:petroleum ether provided 5.23 g (87%) of title compound as a colorless oil.

TLC Silica gel (2:8 ethyl acetate:hexanes) $R_f=0.21$.

IR(neat) 3330, 2964, 2926, 2873, 2858, 1448, 1384, 1107, 1059, 401 cm$^{-1}$.

1H-NMR (CDCl$_3$, 270 MHz): δ 5.10 (m, 3H, H$_2$, H$_6$, H$_{10}$), 3.63 (t, 2H, J=6.5 Hz, H$_{17}$), 1.9–2.2 (m, 10H, H$_1$, H$_4$, H$_5$, H$_8$, H$_9$), 1.68 (s, 3H, H$_{12}$), 1.62 (s, 3H, H$_{15}$), 1.60 (s, 6H, H$_{13}$, H$_{14}$) ppm.*

*H$_{16}$ occurs underneath the resonances for H$_{12}$–H$_{15}$.

Mass Spec (CI-CH$_4$/N$_2$O, +ions) m/e 251 (M+H), 249 (M+H−H$_2$), 137, 123, 109, 69.

B. (E,E)-5,9,13-Trimethyl-4,8,12-tetradecatrien-1-ol, methanesulfonate ester

To a stirred solution of 2.02 g (8.07 mmol) of bishomofarnesol (prepared as described in Example 1, Part A) in 20 mL of dichloromethane at 0° C. was added 2.2 mL (16.1 mmol) of triethylamine followed by 0.69 mL (8.90 mmol) of methanesulfonyl chloride, dropwise over 15 minutes. After stirring for 1.5 hours at 0° C., the reaction was diluted with dichloromethane, washed with 20 mL each of 10% HCl, saturated NaHCO$_3$ and brine, dried (MgSO$_4$) and evaporated to give 2.71 g (100%) of the crude title mesylate as a colorless oil.

TLC Silica gel (CH$_2$Cl$_2$) $R_f=0.46$.

1H NMR (CDCl$_3$, 270 MHz): δ 5.09 (t, 3H, J=6.5 Hz), 4.21 (t, 2H, J=7.0 Hz), 2.99 (s, 3H), 1.9–2.2 (m, 10H), 1.78 (quint, 2H, J=7.0 Hz), 1.65 (s, 3H), 1.61 (s, 3H), 1.60 (s, 6H).

C. (E,E)-14-Iodo-2,6,10-trimethyl-2,6,10-tetradecatriene

The crude Example 1, Part B, mesylate prepared from 441.1 mg (1.76 mmol) of the corresponding alcohol according to the procedure of Example 1, Part B, was dissolved in 5 mL of acetone and treated with 530 mg (3.52 mmol) of sodium iodide. The reaction was allowed to stir for 16 hours at room temperature followed by 5 hours at reflux. The suspension was diluted with hexane and stirred with dilute aqueous sodium bisulfite to discharge to yellow color. The organic layer was washed with water and brine, dried (MgSO$_4$), and evaporated to provide 577 mg of crude product. Flash chromatography on 35 g of silica gel eluted with hexane gave 550.9 mg (87%) of title iodide as a colorless liquid.

TLC Silica gel (hexane) $R_f=0.31$.

1H NMR (CDCl$_3$, 270 MHz): δ 5.09 (m, 3H), 3.16 (t, 2H, J=7.0 Hz), 1.8–2.2 (m, 12H), 1.67 (s, 3H), 1.63 (s, 3H), 1.59 (s, 6H) ppm.

Mass Spec (CI-CH$_4$/N$_2$O, +ions) m/e 361, 359 (M+H), 137.

D. (E,E)-[1-(Ethoxymethylphosphinyl)-6,10,14-trimethyl-5,9,13-pentadecatrienyl]phosphonic acid, diethyl ester To a suspension of 80 mg (3.30 mmol) of NaH in 3 mL of dry DMF and 3 mL of dry THF at 0° C. under argon was added 0.86 g (3.32 mmol) of [(ethoxymethylphosphinyl)methyl]phosphonic acid, diethyl ester (from Example 1, Part A), over 5 minutes to give a yellow solution. The reaction was allowed to warm to room temperature and stir for 0.5 hour when 0.60 g (1.66 mmol) of Example 2, Part C iodide was added in one portion. The reaction mixture was stirred for 18 hours when it was quenched with saturated aqueous NH$_4$Cl solution and diluted with ethyl acetate. The organic fraction was washed with water, brine, dried (Na$_2$SO$_4$) and evaporated to provide a crude yellow oil. Flash chromatography was performed on 75 g of silica gel packed and loaded with ethyl acetate and eluted with 150 mL of ethyl acetate followed by 1:9 ethanol/ethyl acetate collecting in 20 mL fractions. The solvent was removed under reduced pressure to provide 0.40 g (49%) of title compound in the form of a pale yellow oil, a mixture of two diastereomers.

TLC Silica gel (1:9 ethanol:ethyl acetate) $R_f=0.57$.

1H NMR (CDCl$_3$, 270 MHz) δ 5.00 (m, 3H), 4.10 (m, 6H), 2.20 (m, 1H), 2.10–1.70 (m, 10H), 1.60 (s, 3H), 1.59 (d, 2H, J=15.0 Hz), 1.52 (s, 9H), 1.49 (m, 2H), 1.27 (t, 12H, J=7.0 Hz) ppm. Mass Spec (CI-NH$_3$) m/e 491 (M+H), 508 (M+NH$_4$).

E. (E,E)-[1-(Hydroxymethylphosphinyl)-6,10,14-trimethyl-5,9,13-pentadecatrienyl]phosphonic acid, disodium salt To a stirred solution of 0.36 g (0.73 mmol) of Part C compound in 7 mL of dichloromethane at room temperature was added 0.26 g (2.19 mmol) of 2,4,6-collidine followed by 0.45 g (2.92 mmol) of bromotrimethylsilane. The reaction was allowed to stir at room temperature for 6 hours when the solvent was evaporated and the semisolid residue pumped (~1 mm pressure) for 0.5 hour. The residue was dissolved by adding 6 mL of 0.5N NaOH solution (3.0 mmol), diluted with 15 mL of water and then freeze dried. The off white solids were purified by MPLC on a column of CHP20P gel (2.5 cm diam.×15 cm height) eluting with water (150 mL) followed by a gradient created by the gradual addition of 400 mL acetonitrile to a reservoir of 350 mL of water. Approximately 15 mL fractions were collected. The acetonitrile was removed under reduced pressure and the aqueous solution was lyophilized to provide 0.28 g (85%) of title compound as a white lyophilate.

IR (KBr)3441, 2966, 2924, 2856, 1630, 1449, 1292, 1170, 1082, 1041 cm$^{-1}$.

1H NMR (D$_2$O, 400 MHz) δ 5.22 (t, 1H, J=7.0 Hz), 5.12 (q, 2H, J=8.0 Hz), 2.10–1.90 (m, 10H), 1.70 (m, 3H), 1.63 (s, 3H), 1.58 (s, 3H), 1.56 (s, 6H), 1.55 (m, 2H), 1.27 (d, 3H, J=14.0 Hz) ppm.

Mass Spec (FAB) m/e 473 (M+Na), 451 (M+H), 429 (M−Na+2H), 407 (M−2Na+3H).

Anal. Calc'd for C$_{19}$H$_{34}$O$_5$Na$_2$P$_2$+0.85 H$_2$O: C, 49.00; H, 7.73; P, 13.30 Found: C, 49.17; H, 7.77; P, 13.29.

EXAMPLE 3

(E,E)-[1-(Hydroxymethylphosphinyl)-4,8,12-trimethyl-3,7,11-tridecatrienyl]phosphonic acid, disodium salt

A. (E,E)-(3,7,11-Trimethyl-2,6,10-dodecatrienyl)-1-yl bromide

A solution of 1.00 g (4.5 mmol) of E,E-farnesol (Aldrich, further purified by flash chromatography) in 10 mL of distilled Et$_2$O at 0° C. under argon in the dark was treated dropwise with a solution of 195 μL (2.02 mmol, 0.45 eq.) of PBr$_3$ in 2 mL of Et$_2$O. The resultant mixture was stirred at 0° C. for one hour, then quenched with water and separated. The organic phase was washed with 5 mL of H$_2$O, 5 mL of saturated NaHCO$_3$, and 5 mL of brine, dried over Na$_2$SO$_4$ and evaporated to give 1.26 (98%) of crude title bromide as a clear oil.

TLC Silica (2:8 EtOAc:hexane) R$_f$=0.69.

$^1$H NMR (CDCl$_3$, 270 MHz): δ 5.52 (t, 1H, J=8.5 Hz, H$_2$), 5.08 (m, 2H, H$_4$, H$_{10}$), 4.01 (d, 2H, J=8.5 Hz, H$_1$), 1.9–2.2 (m, 8H, H$_4$, H$_5$, H$_8$, H$_9$), 1.73 (s, 3H, H$_{12}$), 1.68 (s, 3H, H$_{15}$), 1.60 (s, 6H, H$_{13}$, H$_{14}$) ppm.

B. (E,E)-[1-(Ethoxymethylphosphinyl)-4,8,12-trimethyl-3,7,11-tridecatrienyl]phosphonic acid, diethyl ester To a stirred solution of 152 mg (6.30 mmol) of NaH in 10 mL of DMF at 0° C. under argon was added dropwise 1.63 g (6.30 mmol) of Example 1, Part A compound. The mixture was stirred for 0.5 hours at 0° C., at which time 1.50 g (5.26 mmol) of Part A bromide was added dropwise. The reaction was stirred at 0° C. for 1 hour, then was diluted with ether and quenched with NH$_4$Cl. The organic layer was washed with water, brine, dried (MgSO$_4$) and evaporated to provide 2.06 g of a pale yellow oil. Flash chromatography was performed on 200 g of silica gel eluted with ethyl acetate (500 mL) followed by a 49.5:49.5:1 mixture of acetone/ethyl acetate/methanol. Pure product fractions were combined and evaporated to provide 970 mg (40%) of title compound as a pale yellow oil.

TLC Silica gel (5:95 methanol/dichloromethane) R$_f$=0.17.

IR (CCl$_4$) 2979, 2922, 2868, 2858, 1443, 1390, 1301, 1243, 1231, 1162, 1097, 1032, 966, 892, 795 cm$^{-1}$.

$^1$H NMR (270 MHz, CDCl$_3$): δ 5.31 (m, 1H), 5.11 (m, 2H), 4.15 (m, 6H), 2.65 (m, 2H), 2.25 (m, 1H), 2.05 (m, 9H), 1.68 (m, 9H), 1.60 (s, 6H), 1.34 (m, 9H) ppm.

MS (CI-NH$_3$, +ions) m/e 463 (M+H).

C. (E,E)-[1-(Hydroxymethylphosphinyl)-4,8,12-trimethyl-3,7,11-tridecatrienyl]phosphonic acid, disodium salt To a stirred solution of 970 mg (2.10 mmol) of Part B compound in 15 mL of dichloromethane at room temperature under argon was added 555 μL (4.20 mmol) of 2,4,6-collidine followed by 1.11 mL (8.40 mmol) of bromotrimethylsilane. The reaction was stirred at room temperature for 18 hours, the solvent was evaporated and the residue was pumped at high vacuum for 1 hour. The remainder was dissolved in 18 mL (9.00 mmol) of 0.5M NaOH and lyophilized. The crude lyophilate was purified by MPLC on a column of CHP20P gel (2.5 cm diameter×18 cm height) eluted with water (fractions 1–15) followed by a gradient created by the gradual addition of 75:25 acetonitrile/water (400 mL) to a reservoir of 400 mL of water. Approximately 15 mL fractions were collected. Pure product fractions were combined, evaporated to remove acetonitrile and lyophilized to provide 820 mg (88%) of title product as a white lyophilate.

IR (KBr) 2969, 2920, 2875, 2858, 1634, 1448, 1293, 1162, 1113, 1085, 1044, 973, 949, 875 cm$^{-1}$.

$^1$H NMR (400 MHz, D$_2$O): δ 5.35 (t, 1H, J=6.7 Hz), 5.18, 5.12 (two t, 2H, J=5.9, 6.9 Hz), 2.45 (sept. 2H, J=7.3 Hz), 2.05, 1.95 (two m, 8H), 1.76 (tt, 1H, J=6.5, 20.5 Hz), 1.63 (s, 3H), 1.61 (s, 3H), 1.56 (s, 6H), 1.28 (d, 3H, J=13.9 Hz) ppm. MS (FAB, +ions) m/e 467 (M+2Na−H), 445 (M+Na), 423 (M+H), 401 (M−Na+2H).

Anal. Calc'd for C$_{17}$H$_{30}$P$_2$O$_5$Na$_2$.0.75 mol H$_2$O Effective MW=435.86 C, 46.85; H, 7.28; P, 14.21 Found: C, 46.67; H, 6.98; P, 14.20.

EXAMPLE 4

1-(Hydroxymethylphosphinyl)-10-methyl-9-undecenylphosphonic acid, tripotassium salt

A. 9-Methyl-8-decen-1-ol

A solution of 55.0 mL (∼52 mmol) of 0.95M Grignard reagent prepared in Example 3, Part A in THF and 15.0 mL of hexamethyl phosphonic triamide (HMPA) at 0° C. was treated dropwise with 1.95 g (13.1 mmol) of phenyl bromide in 8 mL of THF over 10 minutes. After the addition the reaction was allowed to warm to room temperature and stir for 3.5 hours, at which point the reaction was diluted with ether and quenched with 100 mL (100 mmol) of 1M HCl solution. The organic layer was washed two times with NH$_4$Cl solution, dried over MgSO$_4$ and evaporated to provide a pale yellow oil. The oil was purified by flash chromatography performed on 200 g of silica gel eluted with 1:4 ethyl acetate/hexanes to provide 3.50 g of oil and hexanol. The hexanol was removed by distillation under reduced pressure (BP 75° C., ∼20 mm Hg) to leave 1.50 g (67%) of title compound in the form of a colorless oil. This material contains ∼2% of the Sn2' product, which could not be separated.

TLC Silica gel (1:9 ethyl acetate/hexane) R$_f$=0.20.

IR (neat) 3326, 2927, 2855, 1452, 1377, 1059, 625 cm$^{-1}$.

$^1$H NMR (CDCl$_3$, 270 MHz): δ 5.13 (t, 1H, J=7.1 Hz), 3.60 (t, 2H, J=6.4 Hz), 2.40 (m OH, 1H), 1.90 (m, 2H), 1.67 (s, 3H), 1.59 (s, 3H), 1.50 (m, 2H), 1.39 (m, 8H) ppm.

MS (CI-NH$_3$, +ions) m/e 188 (M+NH$_4$).

B. 10-Iodo-2-methyl-2-decene

To a stirred solution of 1.20 g (7.05 mmol) of Part A compound and 2.00 mL (13.70 mmol) of triethylamine in 10 mL of methylene chloride at 0° C. was added 0.67 mL (8.47 mmol) of methanesulfonyl chloride dropwise over 15 minutes. After 1 hour at 0° C. the reaction was diluted with ether and washed with aqueous solutions of NH$_4$Cl, NaHCO$_3$, and brine. The organic layer was dried (MgSO$_4$) and concentrated under reduced pressure to provide the crude mesylate. The residual oil was dissolved in 150 mL of acetone and treated with 4.00 g (28.0 mmol) of NaI and stirred overnight at room temperature. The reaction mixture was diluted with ether and washed with aqueous solutions of Na$_2$SO$_3$ and brine. The organic fraction was dried over MgSO$_4$ and concentrated to provide a yellow oil. The oil was purified by flash chromatography on 100 g of silica gel eluted with hexanes to provide 1.80 g (6.43 mmol, 68% overall yield) of title compound as a colorless oil.

TLC Silica gel (hexanes) R$_f$=0.50.

IR (CCl$_4$ solution) 2926, 2854, 1738, 1641, 1448, 1228 cm$^{-1}$.

$^1$H NMR (270 MHz, CDCl$_3$): δ 5.10 (t, 1H, J=7.0 Hz), 3.15 (t, 2H, J=7.0 Hz), 1.95 (m, 2H), 1.83 (quint., 2H, J=7.5 Hz), 1.66 (s, 3H), 1.57 (s, 3H), 1.35 (m, 2H), 1.30 (m, 6H) ppm.

MS (CI-NH$_3$, +ions) m/e 298 (M+NH$_4$).

C. 1-(Ethoxymethylphosphinyl)-10-methyl-9-undecenylphosphonic acid, diethyl ester A suspension of 130 mg (5.43 mmol) of NaH in 5 mL of dry DMF at 0° C. under argon was treated with 1.40 g (5.43 mmol) of [(ethoxymethylphosphinyl)methyl]phosphonic acid, diethyl ester (Example 1, Part A) over 20 minutes to give a yellow solution. The reaction was allowed to warm to room temperature and stir for 0.5 hours when 0.70 g (2.50 mmol) of Part B iodide was added in one portion. The reaction mixture was stirred for 18 hours when it was quenched with saturated aqueous NH$_4$Cl solution and diluted with ethyl acetate. The organic fraction was washed with brine, dried over Na$_2$SO$_4$ and evaporated to provide a crude yellow oil. Flash chromatography was performed on 100 g of silica gel eluted with 3:97 methanol/methylene chloride (1.5 L) to provide 0.45 g (44%) of title ester as a pale yellow oil.

TLC Silica gel (5:95 methanol/methylene chloride) R$_f$=0.45.

IR (KBr) 2980, 2926, 2855, 1444, 1245, 1029, 965, 896 cm$^{-1}$.

$^1$H NMR (CDCl$_3$, 270 MHz): δ 5.10 (t, 1H, J=7.0 Hz), 4.15 (m, 6H), 2.17 (m, 1H), 2.05-1.80 (m, 4H), 1.68 (s, 3H), 1.67, 1.65 (two d, 3H total, J=14.7 Hz), 1.59 (s, 3H), 1.55 (m, 2H), 1.34 (t, 6H, J=7.0 Hz), 1.29 (m, 11H) ppm.

MS (CI-NH$_4$, +ions) m/e 411 (M+H).

D. 1-(Hydroxymethylphosphinyl)-10-methyl-9-undecenylphosphonic acid, tripotassium salt To a stirred solution of 0.45 g (1.09 mmol) of Part C ester in 5.0 mL of dichloromethane at 0° C. was added 0.29 mL (2.20 mmol) of 2,4,6-collidine followed by 0.58 mL (4.39 mmol) of bromotrimethylsilane. The reaction was allowed to stir at room temperature for 13 hours when the solvent was evaporated and the semisolid residue pumped (~1 mm pressure) for 0.5 hours. The residue was dissolved by adding 4.36 mL (4.36 mmol) of 1N KOH solution, diluting with 15 mL of water and freeze dried. The crude white solids were purified by MPLC on a column of SP207SS gel (2.5 cm diam.×14 cm height) eluting with water (250 mL), followed by a gradient created by the gradual addition of 400 mL acetonitrile to a reservoir of 350 mL of water. Approximately 12 mL fractions were collected. The aqueous solution was filtered and lyophilized to provide 0.37 g (77%) of title salt as a white lyophilate.

IR (KBr) 3418, 2925, 2854, 1636, 1453, 1151, 1077, 966, 875 cm$^{-1}$.

$^1$H NMR (D$_2$O, 400 MHz): δ 5.19 (t, 1H, J=7.3 Hz), 1.93 (m, 2H), 1.63 (s, 3H), 1.60 (m, 3H), 1.56 (s, 3H), 1.45 (m, 2H), 1.30 (d, 3H, J=13.9 Hz), 1.25 (s, 8H) ppm.

Mass Spec. (FAB, +ions) m/e 479 (M+K), 441 (M+H), 403 (M+2H−K).

Anal. Calc'd for C$_{13}$H$_{25}$O$_6$K$_3$P$_2$+2.20 H$_2$O: C, 32.52; H, 6.17; P, 12.90 Found: C, 32.52; H, 6.45; P, 12.93.

EXAMPLE 5

(E)-[4,8-Dimethyl-1-(hydroxymethylphosphinyl)-3,7-nonadienyl]phosphonic acid, trisodium salt A. (E)-[4,8-Dimethyl-1-(ethoxymethylphosphinyl)-3,7-nonadienyl]phosphonic acid, diethyl ester To a stirred solution of 167 mg (6.95 mmol) of NaH in 10 mL of THF at 0° C. under argon was added dropwise 1.79 g (6.95 mmol) of [(ethoxymethylphosphinyl)methyl]phosphonic acid, diethyl ester (from Example 1, Part A). The mixture was stirred for 0.5 hours at 0° C., at which time 1.00 g (5.79 mmol) of Example 6, Part A chloride was added dropwise. The reaction was stirred at 0° C. for 1 hour, room temperature for 18 hours, then was diluted with ether and quenched with saturated NH$_4$Cl. The organic layer was washed with water, brine, dried (MgSO$_4$) and evaporated to provide 1.46 g of a pale yellow oil. Flash chromatography was performed on 150 g of silica gel, eluted with ethyl acetate (500 mL), followed by 49.5:49.5:1 mixture of acetone/ethyl acetate/methanol (1 liter) then a 45:45:10 mixture of acetone/ethyl acetate/methanol (1 liter). Pure product fractions were combined, filtered to remove silica and evaporated to provide 540 mg (24%) of title ester as a pale yellow oil.

TLC Silica gel (49.5:49.5:1 acetone/ethyl acetate/methanol) R$_f$=0.24.

IR (CCl$_4$) 2980, 2926, 1442, 1390, 1246, 1030, 964 cm$^{-1}$.

$^1$H NMR (270 MHz, CDCl$_3$): δ 5.31 (m, 1H), 5.08 (t, 1H, J=6.9 Hz), 4.15 (m, 6H), 2.63 (m, 2H), 2.25 (m, 1H), 2.02 (m, 4H), 1.67, 1.66 (two d, 3H, J=14.6 Hz), 1.67 (s, 3H), 1.65 (s, 3H), 1.60 (s, 3H), 1.30 (m, 9H) ppm.

MS (CI-NH$_3$, +ions) m/e 412 (M+NH$_4$), 395 (M+H).

B. (E)-[4,8-Dimethyl-1-(hydroxymethylphosphinyl)-3,7-nonadienyl]phosphonic acid, trisodium salt To a stirred solution of 530 mg (1.34 mmol) of Part A ester in 15 mL of CH$_2$Cl$_2$ at 0° C. under argon was added 712 μL (2.68 mmol) of bis(trimethylsilyl)trifluoroacetamide followed by 884 μL (6.70 mmol) of bromotrimethylsilane. The reaction was stirred at 0° C. for 0.5 hours, room temperature for 18 hours, the solvent was evaporated and the residue was pumped at high vacuum for 2 hours. The remainder was treated with 4.0 mL (4.0 mmol) of 1M NaOH. The crude solution was purified by MPLC on a column of SP207SS gel (2.5 cm diameter×26.0 cm height) eluted with water (fractions #1–15) followed by a gradient created by the gradual addition of 75:25 acetonitrile/water (400 mL) to a reservoir of 400 mL water. Approximately 15 mL fractions were collected. Pure product fractions were combined, evaporated to remove acetonitrile and lyophilized to provide 400 mg (84%) of title salt as a white lyophilate.

IR (KBr) 2970, 2920, 1631, 1163, 1082, 875 cm$^{-1}$.

$^1$H NMR (400 MHz, D$_2$O): δ 5.37 (t, 1H, J=6.96 Hz), 5.15 (t, 1H, J=6.96 Hz), 2.45 (m, 2H), 2.05, 1.95 (two m, 4H), 1.72 (tt, 1H, J=6.4, 20.5 Hz), 1.63 (s, 3H), 1.60 (s, 3H), 1.57 (s, 3H), 1.29 (d, 3H, J=14.3 Hz) ppm.

MS (FAB, +ions) m/e 399 (M+Na), 377 (M+H), 355 (M−Na+2H).

Anal. Calc'd for C$_{12}$H$_{21}$P$_2$O$_5$Na$_3$.0.25 mol H$_2$O: C, 37.85; H, 5.69; P, 16.27 Found: C, 37.92; H, 6.05; P, 16.48.

EXAMPLE 6

(E)-[1-(Hydroxymethylphosphinyl)-6,10-dimethyl-5,9-undecadienylidene)]phosphonic acid, trisodium salt A. (E)-8-Chloro-2,6-dimethyl-2,6-octadiene To a stirred solution of 30.0 g (0.194 mol) of (E)-3,7-dimethyl-2,6-octadien-1-ol and 28.27 mL (0.213 mol) of 2,4,6-collidine under argon at room temperature was added dropwise 8.23 g (0.194 mol) of lithium chloride in 100 mL of DMF. The mixture was cooled to 0° C. and treated with 16.56 mL (0.213 mmol) of methanesulfonyl chloride dropwise over 10 minutes. The reaction was stirred at 0° C. for 1.5 hours (solid present), then was poured into 500 mL of ice/water. The aqueous solution was washed three times with 200 mL portions of hexane, the organic layers were combined and washed with 5% KHSO$_4$, water, NaHCO$_3$, brine, dried (MgSO$_4$) and evaporated to provide 29.95 g of a pale yellow oil. Rapid flash chromatography was performed on 400 g of silica gel, eluting with 3:9 EtOAc/hexane. Pure product fractions were combined and evaporated to provide 25.20 g (75%) of title compound as a pale yellow oil.

TLC Silica gel (8:1 hexane/EtOAc) R$_f$=0.68.

$^1$H-NMR (CDCl$_3$, 270 MHz): δ 5.44 (m, 1H), 5.08 (m, 1H), 4.09 (d, 2H, J=8.2 Hz), 2.08 (m, 4H), 1.73 (s, 3H), 1.68 (s, 3H), 1.60 (s, 3H) ppm.

B. (E)-(3,7-Dimethyl-2,6-octadienyl)propanedioic acid, diethyl ester

To a stirred solution of 14.68 g (0.611 mol) of NaH (100%) in 400 mL of THF at 0° C. under argon was added dropwise 92.76 mL (0.611 mol) of diethyl malonate in 100 mL of THF over 0.5 hours. This solution was stirred for 0.5 hours at 0° C., at which time 35.20 g (0.204 mol) of Part A chloride in 50 mL of THF was added dropwise over 15 minutes. The reaction gradually warmed to room temperature, stirred for 18 hours then was quenched with 250 mL of saturated NH$_4$Cl and diluted with 250 mL of ether. The organic layer was washed with water, brine, dried (MgSO$_4$) and evaporated to remove solvent and provide 100 g of an oil. The excess diethyl malonate was removed by distillation at 75° C. (1.5 mm) to provide 65 g of title compound also containing some dialkylated product and diethyl malonate.

TLC Silica gel (1:1 Hexane/Ethyl acetate) R$_f$=0.37.

IR (CCl$_4$) 2982, 2926, 2854, 1751, 1734, 1446, 1369, 1332, 1269, 1236, 1209, 1149, 1111, 1095, 1035, 860 cm$^{-1}$.

$^1$H NMR (CDCl$_3$, 270 MHz): δ 5.07 (q, 2H, J=7.1 Hz), 4.18 (q, 2H, J=7.04 Hz), 3.33 (t, 1H, J=7.62 Hz), 2.60 (t, 2H, J=7.33 Hz), 2.04-1.98 (m, 9H), 1.68 (s, 3H), 1.64 (s, 3H), 1.59 (s, 3H), 1.26 (t, 6H, J=7.04 Hz) ppm.

MS (CI-NH$_3$, +ions) m/e 314 (M+NH$_4$), 297 (M+H).

C. (E)-5,9-Dimethyl-4,8-decadienoic acid, ethyl ester

To a solution of 65 g of the crude Part B diester described above, 5.40 mL (0.30 mol) of water and 25.0 g (0.60 mol) of lithium chloride in 250 mL of DMSO was heated to 190° C. and stirred for 9 hours. The reaction was treated with a 1:1 solution of hexane/ether and then washed with water and brine. The organic layer was dried (MgSO$_4$) and evaporated to provide 34.6 g of title compound in the form of a yellow oil. No further purification was performed; the sample was carried on to the next step.

TLC Silica gel (95:5 Hexane/Ethyl acetate) R$_f$=0.30.

$^1$H NMR (CDCl$_3$, 270 MHz): δ 5.00 (m, 2H), 4.04 (q, 2H, J=7.04 Hz), 2.23 (m, 4H), 1.99-1.87 (m, 4H), 1.59 (s, 3H), 1.54 (s, 3H), 1.51 (s, 3H), 1.17 (t, 3H, J=7.04 Hz) ppm.

MS (CI-NH$_3$, +ions) m/e 242 (M+NH$_4$), 225 (M+H).

D. (E)-5,9-Dimethyl-4,8-decadien-1-ol

To a stirred solution of 5.84 g (0.154 mol) of lithium aluminum hydride in 700 mL of ether at 0° C. under argon was added dropwise 34.50 g of crude Part C ester over 20 minutes. The mixture was stirred for 1.5 hours at which time it was quenched by the following: 5.8 mL (0.324 mol) of water, 5.8 mL of 15% NaOH in water and then 17.5 mL (0.973 mol) of water. The granular solution was stirred and dried (MgSO$_4$) for 0.5 hours at which time the mixture was filtered through a celite cake and washed with ether followed by dichloromethane. The filtrate was evaporated to provide 28.16 g of an oil that was distilled using a short-path apparatus (bp 95°-96° C., 0.3 mm) to provide 20.5 g (55% overall from Part A chloride) of title alcohol as a colorless oil.

TLC Silica gel (Dichloromethane) R$_f$=0.11.

IR (CCl$_4$) 3620, 3340, 2966, 2924, 2877, 2856, 2729, 1670, 1446, 1377, 1350, 1278, 1199, 1155, 1107, 1057, 985, 829, 814, 792 cm$^{-1}$.

$^1$H NMR (CDCl$_3$, 270 MHz): δ 5.10 (m, 2H), 3.62 (t, 2H, J=6.45 Hz), 2.11-1.94 (m, 7H), 1.67-1.58 (m, 2H), 1.67 (s, 3H), 1.61 (s, 3H) ppm.

MS (CI-NH$_3$, +ions) m/e 200 (M+NH$_4$), 183 (M+H).

E. (E)-5,9-Dimethyl-4,8-decadien-1-ol, methanesulfonate ester

To a stirred solution of 12.0 g (65.93 mmol) of Part D alcohol in 200 mL of dichloromethane at 0° C. under argon was added 11.95 mL (85.71 mmol) of triethylamine and 6.12 mL (79.12 mmol) of methanesulfonyl chloride. The reaction was stirred for 1 hour then was diluted with ether and washed with 5% KHSO$_4$, saturated NaHCO$_3$ and brine. The organic layer was dried (MgSO$_4$) and evaporated to provide 16.91 g (98%) of title methanesulfonate as a pale yellow oil.

TLC Silica gel (Dichloromethane) R$_f$=0.53.

IR (CCl$_4$) 2963, 2927, 2922, 2882, 2875, 2856, 1455, 1450, 1381, 1363, 1347, 1178, 1007, 969, 957, 929, 793, 785, 758 cm$^{-1}$.

$^1$H NMR (CDCl$_3$, 270 MHz): δ 5.09 (m, 2H), 4.21 (t, 2H, J=6.5 Hz), 2.98 (s, 3H), 2.13-1.99 (m, 6H), 1.79 (quint., 2H, J=6.7 Hz), 1.68 (s, 3H), 1.61 (s, 3H), 1.60 (s, 3H) ppm.

MS (CI-NH$_3$, +ions) m/e 278 (M+NH$_4$).

F. (E)-5,9-Dimethyl-4,8-decadien-1-yl iodide

To a stirred solution of 16.91 g (65.04 mmol) of Part E methanesulfonate in 500 mL of acetone at room temperature under argon was added 39.00 g (260.16 mmol) of sodium iodide. The reaction mixture was refluxed for 3.5 hours, then diluted with 400 mL of a 1:1 mixture of water/hexane. The organic layer was washed with saturated sodium sulfite, dried (MgSO$_4$) and evaporated to provide 17.57 g of a pale yellow oil. The oil residue was filtered through 400 g of silica gel eluting with hexane. The pure product fractions were combined and evaporated to provide 16.86 g (89%) of title iodide as a colorless oil.

TLC Silica gel (Hexane) R$_f$=0.37.

IR (CCl$_4$) 2962, 2924, 2852, 1444, 1375, 1342, 1261, 1226, 1201, 1163, 1107, 983, 873, 835, 819, 761, 742 cm$^{-1}$.

$^1$H NMR (CDCl$_3$, 270 MHz): δ 5.07 (t, 2H, J=7.04 Hz), 3.18 (t, 2H, J=7.04 Hz), 3.14–1.96 (m, 6H), 1.86 (quint., 2H, J=7.04 Hz), 1.68 (s, 3H ), 1.63 (s, 3H ), 1.60 (s, 3H) ppm.

MS (CI-NH$_3$, +ions) m/e 310 (M+NH$_4$).

G. (E)-[1-(Ethoxymethylphosphinyl)-6,10-dimethyl-5,9-undecadienyl]phosphonic acid, diethyl ester To a stirred solution of 99 mg (4.11 mmol) of NaH in 10 mL of DMF at 0° C. under argon was added dropwise 1.06 g (4.11 mmol) of Example 1, Part A [(ethoxymethylphosphinyl)methyl]phosphonic acid, diethyl ester in 2 mL of DMF. The mixture was stirred for 0.5 hours at 0° C., at which time 1.00 g (3.42 mmol) of Part F iodide in 2 mL of DMF was added dropwise. The reaction was stirred at 0° C. for 1 hour, room temperature for 48 hours, then was diluted with ether and quenched with saturated NH$_4$Cl. The organic layer was washed with water, brine, dried (MgSO$_4$) and evaporated to provide 1.52 g of a yellow oil. Flash chromatography was performed on 100 g of silica gel, eluted with a 49.5:49.5:1 mixture of acetone/EtOAc/methanol (1.5 L), followed by a 45:45:10 mixture of acetone/EtOAc/methanol (1.5 L). Pure product fractions were combined and evaporated to provide 600 mg (46%) of title ester, a mixture of diastereomers, as a pale yellow oil.

TLC Silica gel (49.5:49.5:1 acetone/EtOAc/MeOH) R$_f$=0.34.

IR (CCl$_4$) 3474, 2979, 2926, 1231, 1029, 964, 897 cm$^{-1}$.

$^1$H NMR (270 MHz, CDCl$_3$): δ 5.11 (t, 1H, J=7.0 Hz), 5.09 (t, 1H, J=7.0 Hz), 4.15 (m, 6H), 2.30–1.80 (m, 9H), 1.69, 1.66 (two d, 3H, J=14.3 Hz), 1.68 (s, 3H), 1.65 (m, 2H), 1.60 (s, 6H), 1.35, 1.34 (two t, 9H, J=7.0 Hz) ppm.

MS (CI-NH$_3$, +ions) m/e 440 (M+NH$_4$), 423 (M+H).

H. (E)-[1-(Hydroxymethylphosphinyl)-6,10-dimethyl-5,9-undecadienyl]phosphonic acid, trisodium salt To a stirred solution of 600 mg (1.42 mmol) of Part G ester in 14 mL of CH$_2$Cl$_2$ at room temperature under argon was added 469 μL (3.55 mmol) of 2,4,6-collidine followed by 937 μL (7.10 mmol) of bromotrimethylsilane. The reaction was stirred at room temperature for 18 hours, at which time the solvent was evaporated and the residue was pumped on at high vacuum for 2 hours. The remainder was treated with 4.7 mL (4.7 mmol) of 1M NaOH, diluted with water and lyophilized. The crude lyophilate was precipitated by dissolving the sample in 16 mL of water, warming to 50° C., treating the solution with 48 mL of acetone and placing the mixture in an ice bath for 0.5 hours. The solution was decanted from the gelatinous solid and the solid was treated with 8 mL of 3:1 acetone/water. This procedure was performed three times. In each of the washes, the solid was broken up and "mashed" with a spatula in order to aid the washing and solidification. The solid had a final wash with 50 mL of acetone and the fine solid was pumped on by high vacuum for 24 hours to provide 480 mg (83%) of title salt as a white solid.

IR (KBr) 2969, 2927, 2860, 1638, 1449, 1156, 1122, 1076 cm$^{-1}$.

$^1$H NMR (400 MHz, D$_2$O): δ 5.24 (t, 1H, J=6.7 Hz), 5.13 (t, 1H, J=6.7 Hz), 2.30, 1.93 (two m, 6H), 1.70, 1.50 (m, 5H), 1.61 (s, 3H), 1.55 (s, 3H), 1.55 (s, 3H), 1.30 (d, 3H, J=14.0 Hz) ppm.

MS (FAB, +ions) m/e 427 (M+Na), 405 (M+H), 383, (M−Na+2H).

Anal. Calc'd for C$_{14}$H$_{25}$P$_2$O$_5$Na$_3$.1.44 mol H$_2$O: C, 39.09; H, 6.53; P, 14.40 Found: C, 39.09; H, 6.25; P, 14.10.

EXAMPLE 7

(E)-[4-[4-(2,6-Dimethyl-1,5-heptadienyl)phenyl]-1-hydroxymethylphosphinyl)butyl]phosphonic acid, dipotassium salt A. (E)-4-(2,6-Dimethyl-1,5-heptadienyl)benzenemethanol (1) 6-Methyl-5-hepten-1-yne The following procedure was employed: P. A. Jacobi, *Tetrahedron* 1987, 43, 5475–5488.

To a suspension of 12.48 g (128.8 mmol) of 95% lithium acetylide-ethylenediamine complex in 64 mL of freshly distilled dimethyl sulfoxide under argon between 5°–10° C. was added 20 g (122.6 mmol) of 5-bromo-2-methyl-2-pentene dropwise over 30 minutes with vigorous stirring. After the addition was complete, the mixture was allowed to warm to room temperature gradually over 1 hour and then stirred at room temperature for 1 hour. The reaction was cooled to about 15° C. and quenched by the slow addition of 25 mL of water. The reaction mixture was then distilled under reduced pressure using a short path distillation head and cooling the condenser with a 50:50 mixture of water:ethylene glycol from a circulating cold bath at −20° C. The product was collected at a boiling point range of 28°–37° C., pressure 90 mm Hg with an oil bath temperature of 60°–62° C. The distillation was run under these parameters for 1 hour and then the pressure was carefully lowered to 60 mm Hg and the distillation was continued for 1.5 hours to provide 9.28 g of a clear, colorless oil. This material was fractionally distilled at 1 atmosphere to provide 4.01 g (30%) of 2-methyl-2,3-pentadiene (bp 85°–90° C.), followed by 4.43 g (33%) of the desired title (1) eneyne (bp 120°–125° C.) as a colorless liquid.

$^1$H-NMR (CDCl$_3$, 270 MHz): δ 5.17 (m, 1H, H$_{10}$), 2.19 (m, 4H, H$_8$, H$_9$), 1.93 (t, 1H, J=2.3 Hz, H$_6$), 1.70 (s, 3H, H$_{12}$), 1.62 (s, 3H, H$_{13}$) ppm.

(2) (E)-1-Iodo-2,6-dimethyl-1,5-heptadiene

The following procedure of Negishi was used for the reaction: E. Negishi, *J. Am. Chem. Soc.* 985, 107, 6639–6647.

To a stirred solution of 4.13 g (13.86 mmol) of 98% zirconocene dichloride in 35 mL of dichloromethane under argon at room temperature was added 13.9 mL (27.72 mmol) of 2.0M trimethyl aluminum in hexanes. The mixture was allowed to stir at room temperature for 0.5 hours resulting in a lemon-yellow solution to which 1.5 g (13.86 mmol) of Part (1) compound was added neat and the reaction was allowed to stir at room temperature for 24 hours. The yellow solution was cooled to −30° C. and 4.22 g (16.6 mmol) of iodine in 15 mL of THF was added dropwise over 10 minutes. Upon addition of the iodine, the solution color turned orange-brown for a few minutes and then turned orange-yellow with precipitated solids. The mixture was allowed to warm to 0° C. and stir for 0.5 hours when it was quenched with methanol and diluted with ether. The organic layer was washed with aqueous Na$_2$S$_2$O$_3$, dried over MgSO$_4$ and filtered. The solvent was removed by distillation using a fractionating column (bp 38°–40° C./1 atmosphere) to provide a dark yellow oil as the pot residue. The remaining port residue was further purified by bulb-to-bulb distillation (115° C./2 mm) to provide 2.32 g (67%) of title iodide as a pale yellow oil.

$^1$H-NMR (CDCl$_3$, 270 MHz): δ 5.87 (s, 1H, H$_6$), 5.05 (m, 1H, H$_{10}$), 2.15 (m, 4H, H$_8$, H$_9$), 1.84 (s, 3H, H$_{14}$), 1.68 (s, 3H, H$_{12}$), 1.60 (s, 3H, H$_{13}$) ppm.

(3) (E)-4-(2,6-Dimethyl-1,5-heptadienyl)benzoic acid, methyl ester

To 10 mL of THF under argon at −78° C. was added 6.1 mL (10.3 mmol, 2.4 equiv) of 1.7M t-butyllithium in pentane resulting in a yellow solution, to which 1.075 g (4.29 mmol, 1 equiv) of Part (2) iodide in 10 mL of THF was added dropwise over 5 minutes. After the addition, the reaction was allowed to stir at −78° C. for 0.5 hours and then warm to 0° C. for 0.5 hours. Zinc chloride (702 mg, 5.16 mmol, 1.2 equiv, fuse-dried under vacuum three times) in 7 mL of THF was added via cannula to give a very pale yellow solution, which was allowed to stir at 0° C. for 1 hour.

A 100 mL flask was charged with 248 mg (5 mol %) of tetrakis(triphenylphosphine) palladium and 804 mg (3.07 mmol) of methyl 4-iodobenzoate in an argon filled glove bag. A volume of 10 mL of THF was added and the suspension was cooled to 0° C. when the zinc intermediate prepared above was added via cannula. The mixture was allowed to warm to room temperature and stir for 1.5 hours when it was diluted with ether and quenched by the addition of 1N HCl solution. The organic layer was washed with water, saturated NaHCO$_3$, brine, dried over MgSO$_4$ and evaporated to provide 1.29 g of an orange-yellow oily solid. Flash chromatography was performed on 130 g of silica gel packed and loaded with 5:1 hexane/ toluene and eluted with 3:1 hexane/toluene collecting 30 mL fractions. Fractions 84 to 106 were combined and evaporated to provide 602 mg (76%) of title esters as a clear, colorless oil.

TLC Silica gel (9:1 hexane/EtOAc) R$_f$=0.47.

IR (CCl$_4$) 2968, 2914, 1724, 1606, 1435, 1309, 1277, 1192, 1178 cm$^{-1}$.

$^1$H-NMR (CDCl$_3$, 270 MHz): δ 7.97 (d, 2H, J=8.2 Hz, H$_3$), 7.28 (d, 2H, J=8.2 Hz, H$_4$), 6.28 (s, 1H, H$_6$), 5.15 (m, 1H, H$_{10}$), 3.89 (s, 3H, OCH$_3$), 2.20 (m, 4H, H$_8$, H$_9$), 1.87 (d, 3H, J=1.2 Hz, H$_{14}$), 1.70 (s, 3H, H$_{12}$), 1.63 (s, 3H, H$_{13}$) ppm.

MS (CI-NH$_3$, +ions) m/e 276 (M+NH$_4$), 259 (M+H).

(4) (E)-4-(2,6-Dimethyl-1,5-heptadienyl)benzenemethanol

To 133 mg (3.49 mmol) of lithium aluminum hydride under argon at 0° C. suspended in 10 mL of dry ether was added 602 mg (2.32 mmol) of Part (3) ester in 15 mL of dry ether dropwise over 5 minutes. The reaction was allowed to stir at 0° C. for 0.5 hours when it was quenched by the addition of 0.14 mL of water, 0.14 mL of 15% NaOH solution and then with 0.42 mL of water. After stirring for 0.5 hours, Na$_2$SO$_4$ was added and the slurry was allowed to stir for 1 hour before filtering through a pad of celite washing copiously with ether. Evaporation provided 519 mg (97%) of a pale yellow oil. The crude material was combined with 324 mg of crude product from a previous reduction on 371 mg (1.44 mmol) of Part (3) ester to provide 843 mg of crude product. Flash chromatography was performed on 85 g of silica gel packed and loaded with 15:1 hexane/ EtOAc and eluted with 9:1 hexane/EtOAc collecting 30 mL fractions. Fractions 34 to 85 were combined and evaporated to provide 802 mg (93%) of title alcohol as a clear, colorless oil.

TLC Silica gel (12:1 dichloromethane/EtOAc) R$_f$=0.36.

IR (CCl$_4$) 3617, 3400, 2967, 2928, 2874, 2858, 1718, 1449, 1414, 1377, 1032, 1013, 795 cm$^{-1}$.

$^1$H-NMR (CDCl$_3$, 270 MHz): δ 7.27 (d, 2H, J=8.2 Hz, H$_3$), 7.20 (d, 2H, J=8.2 Hz, H$_4$), 6.25 (s, 1H, H$_6$), 5.16 (m, 1H, H$_{10}$), 4.60 (s, 2H, H$_1$), 2.18 (m, 4H, H$_8$, H$_9$), 1.85 (d, 3H, J=1.2 Hz, H$_{14}$), 1.70 (s, 3H, H$_{12}$), 1.63 (s, 3H, H$_{13}$) ppm.

MS (CI-NH$_3$, +ions) m/e 478 (2M+NH$_4$), 460 (2M), 248 (M+NH$_4$), 230 (M), 213 (M+H−H$_2$O).

Analysis Calc'd for C$_{16}$H$_{22}$O (M.W.=230.36): C, 83.43; H, 9.63 Found: C, 83.18; H, 9.73.

B. (E)-1-(Bromomethyl)-4-(2,6-dimethyl-1,5-heptadienyl)benzene

To a stirred solution of 1 g (4.34 mmol) of Part A alcohol in 50 mL of dichloromethane under argon at −30° C. was added 1.36 g (5.21 mmol) of triphenylphosphine followed by 850 mg (4.77 mmol) of n-bromosuccinimide and the reaction was allowed to stir at −30° C. for 1 hour when it was concentrated to about 5 mL. Flash chromatography was performed on 125 g of silica gel packed, loaded and eluted with 1% EtOAc/pentane collecting 10 mL fractions. Fractions 14 to 40 were combined and evaporated to provide 863 mg (69%) of title compound in the form of a clear colorless oil.

TLC Silica gel (9:1 Pentane/EtOAc) R$_f$=0.59.

IR (CCl$_4$) 2969, 2930, 2857, 1711, 1608, 1510, 1450, 1377, 1229, 1202, 775 cm$^{-1}$.

$^1$NMR (CDCl$_3$, 270 MHz) δ 7.32 (d, 2H, J=8.2 Hz), 7.19 (d, 2H, J=8.2 Hz), 6.23 (s, 1H), 5.15 (m, 1H), 4.49 (s, 2H), 2.19 (m, 4H), 1.85 (s, 3H), 1.70 (s, 3H), 1.63 (s, 3H), ppm.

C. (E)-4-(2,6-Dimethyl-1,5-heptadienyl)benzenepropanoic acid, 1,1-dimethylethyl ester To a stirred solution of 0.62 mL (4.44 mmol) of freshly distilled diisopropylamine in 4 mL of THF under argon at −78° C. was added 1.85 mL (2.96 mmol) of 1.6M n-butyllithium in hexanes to give a pale yellow solution. The solution was allowed to warm to 0° C. for 15 minutes and then cooled again to −78° C. when 0.40 mL (2.96 mmol) of t-butyl acetate was added neat. After an additional 15 minutes, 1.05 mL (6.07 mmol) of HMPA followed by 853 mg (2.96 mmol) of Part B bromide in 5 mL of dry THF was added dropwise over 5 minutes. The reaction was allowed to stir at −78° C. for 1 hour when it was diluted with ether and quenched by the addition of saturated NH$_4$Cl solution. The organic layer was washed with water, brine, dried over MgSO$_4$ and evaporated to provide 994 mg of a clear colorless oil. Flash chromatography was performed on 100 g of silica gel packed and loaded with 2% EtOAc/hexane and eluted with 3% EtOAc/hexane collecting 30 mL fractions. Fractions 18 to 25 were combined and evaporated to provide 850 mg (87%) of title compound in the form of a clear colorless oil.

TLC Silica gel (9:1 hexane/EtOAc) R$_f$=0.53.

IR (CCL$_4$) 2969, 2928, 2874, 1730, 1512, 1452, 1368, 1269, 1146, 849 cm$^{-1}$.

$^1$H NMR (270 MHz, CDCl$_3$): δ 7.14 (s, 4H), 6.23 (s, 1H), 5.15 (m, 1H), 2.88 (t, 2H, J=7 Hz), 2.52 (t, 2H, J=7 Hz), 2.17 (m, 4H), 1.85 (s, 3H), 1.70 (s, 3H), 1.63 (s. 3H), 1.41 (s, 9H) ppm.

MS (CI-NH$_3$, CI, +ions) m/e 346 (M+NH$_4$).

Anal. Calc'd for C$_{22}$H$_{32}$O$_2$: C, 80.44; H, 9.82 Found: C, 80.51; H, 9.76.

D. (E)-4-(2,6-Dimethyl-1,5-heptadienyl)benzenepropanol

To 215 mg (5.66 mmol) of lithium aluminum hydride under argon at 0° C. was added 10 mL of dry ether followed by 1.24 g (3.77 mmol) of Part C compound in 20 mL of dry ether dropwise over 10 minutes. The reaction was allowed to stir at 0° for 0.5 hours when it was quenched by the addition of 0.23 mL of H$_2$O, 0.23 mL of 15% NaOH solution and then with 0.68 mL of H$_2$O. After stirring for 0.5 hours, Na$_2$SO$_4$ was added and the mixture was allowed to stir for 1 hour before filtering through a pad of Celite washing copiously with ether. Evaporation provided 973 mg of a pale yellow oil. Flash chromatography was performed on 100 g of silica gel packed and loaded with 7:1 hexane/EtOAc and eluted with 6:1 hexane/EtOAc collecting 30 mL fractions. Fractions 25 to 42 were combined and evaporated to provide 876 mg (90%) of title compound in the form of a clear colorless oil.

TLC Silica gel (4:1 hexane/EtOAc) R$_f$=0.19.

IR (CCl$_4$) 3346, 2928, 2857, 1670, 1510, 1447, 1377, 1059 cm$^{-1}$.

$^1$H NMR (270 MHz, CDCl$_3$): δ 7.15 (m, 4H), 6.23 (s, 1H), 5.16 (m, 1H), 3.66 (br t, 2H, J=6.5 Hz), 2.68 (t, 2H, J=7.6 Hz), 2.18 (m, 4H), 1.89 (m, 2H), 1.85 (s, 3H), 1.70 (s, 3H), 1.63 (s, 3H), 1.54 (br s, 1H) ppm.

MS (CI-NH$_3$, CI, +ions) m/e 276 (M+NH$_4$).

Anal. Calc'd for C$_{18}$H$_{26}$O: C, 83.67; H, 10.14 Found: C, 83.79; H, 10.01.

E. (E)-1-(2,6-Dimethyl-1,5-heptadienyl)-4-(3-iodopropyl)benzene

To a stirred solution of 300 mg (1.16 mmol) of Part D compound, 336 mg (1.28 mmol) of triphenylphosphine and 166 mg (2.44 mmol) of imidazole in 6 mL of THF under argon at room temperature was added 294 mg (1.16 mmol) of iodine in 6 mL of THF dropwise over 5 minutes. Upon addition the clear solution would turn yellow and then quickly back to clear. Near the end of the addition the color remained pale yellow. After addition the reaction was complete by TLC. The reaction was diluted with ether and washed with water, saturated Na$_2$S$_2$O$_2$, brine, dried over MgSO$_4$ and evaporated to provide an oily white solid. Flash chromatography was performed on 50 g of silica gel packed, loaded and eluted with hexane collecting 15 mL fractions. Fractions 7 to 24 were combined and evaporated to provide 342 mg (80%) of title compound in the form of a clear colorless oil.

TLC Silica gel (4:1 hexane/EtOAc) R$_f$=0.65.

$^1$H NMR (270 MHz, CDCl$_3$): δ 7.15 (m, 2H), 6.23 (s, 1H), 5.16 (m, 1H), 3.17 (t, 2H, J=7 Hz), 2.70 (t, 2H, J=7 Hz), 2.19 (m, 4H), 2.14 (quint., 2H, J=7 Hz), 1.86 (s, 3H), 1.70 (s, 3H), 1.63 (s, 3H) ppm.

F. (E)-[4-[4-(2,6-Dimethyl-1,5-heptadienyl)phenyl]-1-(ethoxymethylphosphinyl)butyl]phosphonic acid, diethyl ester To 149 mg (3.72 mmol) of 60% NaH in mineral oil under argon at 0° C. was added 3 mL of DMF and 1 g (3.87 mmol) of Example 1, Part A [(ethoxymethylphosphinyl)methyl]phosphonic acid, diethyl ester, in 4 mL of DMF was added dropwise over 10 minutes with much gas evolution. The reaction was allowed to warm to room temperature and stir for 0.5 hours when 549 mg (1.49 mmol) of Part E iodide in 3 mL of DMF was added and the reaction was allowed to stir at room temperature. The reaction was diluted with ether and quenched by the addition of saturated NH$_4$Cl solution. The organic layer was washed with water, brine, dried over MgSO$_4$ and evaporated to provide 870 mg of a pale yellow oil. Flash chromatography was performed on 130 g of silica gel packed, loaded and eluted with 2:98 CH$_3$OH/CH$_2$Cl$_2$ collecting 30 mL fractions. Fractions 37 to 78 were combined and evaporated to provide 424 mg (57%) of title ester as a pale yellow oil.

TLC Silica gel (5:95 CH$_3$OH/CH$_2$Cl$_2$) R$_f$=0.24.

IR (CCl$_4$) 2978, 2928, 1452, 1231, 1026, 966, 897 cm$^{-1}$.

$^1$H NMR (270 MHz, CDCl$_3$): δ 7.13 (m, 4H), 6.22 (s, 1H), 5.12 (m, 1H), 4.10 (m, 6H), 2.62 (m, 2H), 2.10–2.30 (m, 5H), 1.92 (m, 4H), 1.84 (s, 3H), 1.70 (s, 3H), 1.66 (d, 3H, J=15 Hz), 1.63 (s, 3H), 1.30 (m, 9H total) ppm.

MS (CI +ions) m/e 499 (M+H).

Anal. Calc'd for C$_{26}$H$_{44}$O$_5$P$_2$.0.25 H$_2$O: C, 62.07; H, 8.92; P, 12.31 Found: C, 62.18; H, 9.22; P, 12.53.

G. (E)-[4-[4-(2,6-Dimethyl-1,5-heptadienyl)phenyl]-1-(hydroxymethylphosphinyl)butyl]phosphonic acid, dipotassium salt To a stirred solution of 424 mg (0.850 mmol) of Part F ester in 6 mL of dichloromethane under argon at 0° C. was added 0.34 mL (2.55 mmol) of 2,4,6-collidine followed by 0.67 mL (5.10 mmol) of bromotrimethylsilane and the reaction was allowed to warm to room temperature and stir for 20 hours. The solvent was evaporated and pumped at high vacuum for 1 hour. The remainder was dissolved in 5.1 mL (5.10 mmol) of 1M KOH, stirred for 1 hour, diluted with water and lyophilized to provide 874 mg of crude lyophilate. The crude material was purified by MPLC on a column of SP207SS (2.5 cm diameter×18 cm height) eluted with water fractions (1 to 12) followed by a gradient created by the gradual addition of 500 mL of a 70:30 CH$_3$CN/H$_2$O to a reservoir of 450 mL of water. Approximately 5 mL fractions were collected and the pH at fraction 12 was pH=10. Fractions 60 to 67 were combined, the acetonitrile was evaporated at reduced pressure and the aqueous solution was lyophilized to provide 156 mg (35%) of title salt as a dense white lyophilate.

IR (KBr) 3397, 2967, 2926, 1651, 1292, 1163, 1074, 879 cm$^{-1}$.

$^1$H NMR (400 MHz, D$_2$O): δ 7.25 (d, 2H, J=8 Hz), 7.22 (d, 2H, J=8 Hz), 6.25 (s, 1H), 5.20 (m, 1H), 2.61 (t, 2H, J=7 Hz), 2.16 (m, 4H), 1.82 (s, 3H), 1.65 (s, 3H), 1.60–1.90 (m, 5H total), 1.59 (s, 3H), 1.26 (d, 3H, J=14 Hz) ppm.

MS (FAB, +ions) m/e 529 (M+K), 491 (M+H), 453 (M+2H−K).

Anal. Calc'd for C$_{20}$H$_{30}$O$_5$P$_2$K$_2$.0.55 H$_2$O.0.25 CH$_3$CO$_2$H: C, 47.76; H, 6.28; P, 12.02 Found: C, 47.44; H, 6.22; P, 12.39.

EXAMPLE 8

(E)-[1-(Hydroxymethylphosphinyl)-7,11-dimethyl-6,10-dodecadienyl]phosphonic acid, dipotassium salt A. (E)-6,10-Dimethyl-5,9-undecadien-1-ol A solution of 198 mL (58.0 mmol) of 0.29M Example 1, Part B-(2) Grignard reagent in THF and 48 mL (275.9 mmol) of HMPA at 0° C. under argon was treated dropwise with 2.0 g (11.6 mmol) of Example 6, Part A chloride in 20 mL of THF. After addition, the reaction was allowed to warm to room temperature for 2 hours, at which point the reaction was diluted with 1:1 hexane/ether and quenched with 1N HCl solution. The organic layer was washed with 1N HCl followed by water, saturated sodium bicarbonate, brine, dried over MgSO$_4$ and evaporated to provide 3.59 g of crude oil.

Flash chromatography was performed on 360 g of silica gel packed and loaded with 10:1 hexane/EtOAc and eluted with 7:1 hexane/ EtOAc collecting 30 mL fractions. Fractions 32 to 49 were combined and evaporated to provide 1.68 g (74%) of title compound in the form of an oil.

TLC Silica gel (7:1 hexane/EtOAc) $R_f=0.19$.

$^1$H-NMR (CDCl$_3$, 270 MHz): δ 5.11 (m, 2H), 3.61 (t, 2H, J=6.45 Hz), 2.03 (m, 6H), 1.68 (s, 3H), 1.59 (s, 6H), 1.5–1.6 (m, 2H), 1.41 (m, 2H) ppm.

B. (E)-6,10-Dimethyl-5,9-undecadien-1-yl iodide

A solution of 1.80 g (9.20 mmol) of Part A alcohol in 50 mL of methylene chloride and 2.00 mL (14.3 mmol) of triethylamine at 0° C. was treated with 1.14 g (10.00 mmol) of methanesulfonyl chloride dropwise over 0.2 hour. The reaction mixture was stirred for 1.0 hours when it was quenched with saturated aqueous NH$_4$Cl solution and diluted with ether. The organic fraction was washed with saturated NaHCO$_3$, brine, dried (Na$_2$SO$_4$) and evaporated to provide a crude colorless oil. The crude mesylate (~9.0 mmol) was diluted with 50 mL of acetone and treated with 4.05 g (27.00 mmol) of NaI, refluxed for 5 hours, and cooled to room temperature. The mixture was diluted with 250 mL of ether and extracted with NaHSO$_3$, brine, dried (MgSO$_4$) and concentrated to provide a pale yellow oil. The oil was purified by flash chromatography (180 g of silica gel) eluting with hexane to provide 2.60 g (85%) of title iodide as a colorless oil.

TLC Silica gel (hexane) $R_f=0.55$.

IR (neat) 2963, 2926, 2854, 1448, 1377, 1221, 1107 cm$^{-1}$.

$^1$H NMR (CDCl$_3$, 270 MHz): δ 5.10 (m, 2H), 3.20 (t, 2H, J=6.5 Hz), 2.05 (m, 6H), 1.80 (quint., 2H, J=6.0 Hz), 1.60 (s, 3H), 1.55 (s, 6H), 1.45 (m, 2H) ppm.

Mass Spec (CI-NH$_3$, +ions) m/e 306 (M), 324 (M+NH$_4$).

C. (E)-[1-(Ethoxymethylphosphinyl)-7,11-dimethyl-6,10-dodecadienyl]phosphonic acid, diethyl ester To a suspension of 144 mg (6.00 mmol) of NaH in 5 mL of dry DMF at 0° C. under argon was added 1.54 g (6.00 mmol) of Example 1, Part A [(ethoxymethylphosphinyl)methyl]phosphonic acid, diethyl ester, over 15 minutes to give a yellow solution. The reaction was allowed to warm to room temperature and stir for 0.5 hours when 0.63 g (2.00 mmol) of Part B iodide was added in one portion. The reaction mixture was stirred for 18 hours when it was quenched with saturated aqueous NH$_4$Cl solution and diluted with ethyl acetate. The organic fraction was washed with water, brine, dried (Na$_2$SO$_4$) and evaporated to provide a crude yellow oil. Flash chromatography was performed on 75 g of silica gel eluted with 4:96 methanol/methylene chloride to provide 0.45 g (50%) of title ester as a pale yellow oil.

TLC Silica gel (1:9 ethanol:ethyl acetate) $R_f=0.25$.

IR (neat) 2980, 2929, 2859, 1650, 1445, 1378, 1235, 1031, 966, 894 cm$^{-1}$.

$^1$H NMR (CDCl$_3$, 270 MHz): δ 5.15 (q, 2H, J=5.9 Hz), 4.20 (m, 6H), 2.17 (m, 1H), 2.00 (m, 8H), 1.68 (s, 3H), 1.67, 1.65 (two d, 3H, J=14.3 Hz), 1.59 (s, 6H), 1.57 (m, 2H), 1.37 (m, 2H), 1.34 (t, 6H, J=7.0 Hz), 1.32 (t, 3H, J=7.0 Hz) ppm.

Mass Spec (CI-NH$_3$, +ions) m/e 454 (M+NH$_4$), 437 (M+H).

D. (E)-[1-(Hydroxymethylphosphinyl)-7,11-dimethyl-6,10-dodecadienyl]phosphonic acid, dipotassium salt To a stirred solution of 0.40 g (0.89 mmol) of Part C ester in 7 mL of dichloromethane at room temperature was added 0.21 g (1.78 mmol) of 2,4,6-collidine followed by 0.68 g (4.48 mmol) of bromotrimethylsilane. The reaction was allowed to stir at room temperature for 14 hours when the solvent was evaporated and the semisolid residue pumped (~1 mm pressure) for 0.5 hours. The residue was dissolved by adding 3.0 mL of 1N KOH solution (3.0 mmol) then diluting with 15 mL of water. The solution was freeze dried to provide off white solids. The solids were purified by MPLC on a column of SP207SS gel (2.5 cm diam.×23 cm height) eluting with water (150 mL) followed by a gradient created by the gradual addition of 400 mL of acetonitrile to a reservoir of 350 mL of water. Approximately 15 mL fractions were collected. The acetonitrile was removed under reduced pressure and the aqueous solution was lyophilized to provide 0.33 g (86%) of title salt as a white lyophilate.

IR (KBr) 3457, 2980, 2926, 2855, 1650, 1445, 1302, 1245, 1163, 1097, 1029, 964 cm$^{-1}$.

$^1$H NMR (D$_2$O, 400 MHz): δ 5.21 (t, 1H, J=7.0 Hz), 5.14 (t, 1H, J=7.0 Hz), 2.05 (m, 2H), 2.00 (m, 4H), 1.70 (m, 3H), 1.63 (s, 3H), 1.57 (s, 6H), 1.50 (m, 2H), 1.30 (m, 2H), 1.28 (d, 3H, J=14.0 Hz) ppm.

Mass Spec (FAB, +ions) m/e 505 (M+2K−H), 467 (M+K) 429 (M+H) 411 (M+H−H$_2$O) 391 (M−K+2H)

Anal. Calc'd for C$_{15}$H$_{28}$O$_5$K$_2$P$_2$+0.80 H$_2$O: C, 40.67; H, 6.74; P, 13.99 Found: C, 40.35; H, 6.75; P, 14.33.

EXAMPLE 9

(Z)-[1-(Hydroxymethylphosphinyl)-6,10-dimethyl-5,9-undecadienyl]phosphonic acid, disodium salt A. (Z)-10-Iodo-2,6-dimethyl-2,6-decadiene (1) (Z)-8-Chloro-2,6-dimethyl-2,6-octadiene To a stirred solution of 10.0 g (64.83 mmol) of (Z)-3,7-dimethyl-2,6-octadien-1-ol and 9.42 mL (71.31 mmol) of 2,4,6-collidine under argon at room temperature was added dropwise 2.74 g (64.83 mmol) of lithium chloride in 30 mL of DMF. The mixture was cooled to 0° C. and treated with 5.52 mL (71.31 mmol) of methanesulfonyl chloride dropwise over 10 minutes. The reaction was stirred at 0° C. for 4 hours (solid present), then was poured into 300 mL of ice/water. The aqueous solution was washed three times with 200 mL portions of hexane. The organic layers were combined and washed with 5% KHSO$_4$, water, saturated NaHCO$_3$, brine, dried (MgSO$_4$) and evaporated to provide 9.48 g (85%) of title chloride as a pale yellow oil.

TLC Silica gel (8:1 hexanes/ethyl acetate) $R_f=0.44$.

$^1$H NMR (270 MHz, CDCl$_3$): δ 5.45 (t, 1H, J=6.0 Hz), 5.11 (m, 1H), 4.08 (d, 2H, J=7.0 Hz), 2.11 (m, 4H), 1.77 (s, 3H), 1.69 (s, 3H), 1.62 (s, 3H) ppm.

(2) (Z)-(3,7-Dimethyl-2,6-octadienyl)propanedioic acid, diethyl ester

To a stirred solution of 3.96 g (0.165 mol) of NaH in 100 mL of THF at 0° C. under argon was added dropwise 25.10 mL (0.165 mol) of diethyl malonate over 15 minutes. The solution was stirred for 0.5 hours at 0° C., at which time 9.50 g (0.055 mol) of Part (1) chloride in 50 mL of THF was added dropwise over 15 minutes. The reaction gradually warmed and was stirred for 18 hours at room temperature, then was diluted with ether and quenched with saturated NH$_4$Cl. The organic layer was washed with water, brine, dried (MgSO$_4$) and concentrated to provide a pale yellow oil. The excess diethyl malonate was distilled away (1.5 mm Hg, 75° C.)

from the title diester providing 14.10 g (87%) of title ester as a colorless oil.

TLC Silica gel (9:1 hexanes/ethyl acetate) $R_f=0.44$.

$^1$H NMR (270 MHz, CDCl$_3$): δ 5.10 (m, 2H), 4.18 (q, 4H, J=7.0 Hz), 3.30 (t, 1H, J=7.6 Hz), 2.59 (t, 2H, J=7.6 Hz), 2.06 (m, 4H), 1.68 (s, 6H), 1.61 (s, 3H), 1.25 (t, 6H, J=7.0 Hz) ppm.

(3) (Z)-5,9-Dimethyl-4,8-decadienoic acid, ethyl ester

A stirred solution of 14.10 g (47.60 mmol) of Part (2) diester, 1.0 mL (57.12 mmol) of water and 4.85 9 (114.3 mmol) of lithium chloride in 50 mL of DMSO was heated to 190° C. for 3 hours. The reaction was cooled to room temperature and diluted with 500 mL of a 1:1 solution of hexane/ether, then washed with water, brine and dried (MgSO$_4$). The organic layer was concentrated to provide 6.40 g (28.6 mol) of title ester as a pale yellow oil.

TLC Silica gel (95:5 hexanes/ethyl acetate) $R_f=0.34$.

$^1$H NMR (270 MHz, CDCl$_3$): δ 5.11 (m, 2H), 4.12 (q, 2H, J=7.0 Hz), 2.30 (m, 2H), 2.05 (m, 2H), 1.68 (s, 6H), 1.61 (s, 3H), 1.25 (t, 3H, J=7.0 Hz) ppm.

MS (CI-NH$_3$, +ions) m/e 242 (M+NH$_4$), 225 (M+H).

(4) (Z)-5,9-Dimethyl-4,8-decadien-1-ol

To a stirred solution of 1.10 g (28.60 mmol) of lithium aluminum hydride in 125.0 mL of ether at 0° C. under argon was added dropwise 6.40 g (28.60 mmol) of Part (3) ester in 35.0 mL of ether over 10 minutes. The mixture stirred for 1.5 hours and was quenched by the following: 1.10 mL of water, 1.10 mL of 15% NaOH and 3.30 mL of water. The resulting suspension was dried (MgSO$_4$) and filtered through a Celite cake. The filtrate was concentrated to provide 5.80 g of a yellow oil. The oil was purified by short path distillation (0.5 mm-Hg; 142°-145° C.) to provide 3.26 g (63% overall from Part A chloride) of title alcohol as a colorless oil.

TLC Silica gel (9:1 hexanes/ethyl acetate) $R_f=0.20$.

$^1$H NMR (270 MHz, CDCl$_3$): δ 5.12 (m, 2H), 3.64 (q, 2H, J=6.5 Hz), 2.05 (m, 6H), 1.70 (s, 3H), 1.69 (s, 3H), 1.61 (s, 3H), 1.60 (m, 2H) ppm.

(5) Methanesulfonic acid, (Z)-(5,9-dimethyl-4,8-decadienyl) ester

To a stirred solution of 3.26 g (17.91 mmol) of Part (4) alcohol in 50 mL of dichloromethane at 0° C. under argon was added 3.25 mL (23.28 mmol) of triethylamine and 1.66 mL (21.49 mmol) of methanesulfonyl chloride. The reaction was stirred for 2 hours at which time it was diluted with ether and washed with 5% KHSO$_4$, saturated NaHCO$_3$ and brine. The organic layer was dried (MgSO$_4$) and evaporated to provide 4.20 g (91%) of sulfonate as a pale yellow oil.

TLC Silica gel (CH$_2$Cl$_2$) $R_f=0.63$.

$^1$H NMR (270 MHz, CDCl$_3$): δ 5.10 (m, 2H), 4.21 (t, 2H, J=6.5 Hz), 2.99 (s, 3H), 2.10 (q, 2H, J=7.6 Hz), 2.04 (m, 4H), 1.78 (quint, 2H, J=7.0 Hz), 1.70 (s, 3H), 1.68 (s, 3H), 1.61 (s, 3H) ppm.

(6) (Z)-10-Iodo-2,6-dimethyl-2,6-decadiene

To a stirred solution of 4.20 g (16.15 mmol) of Part (5) sulfonate in 100 mL of acetone at room temperature under argon was added 9.68 g (64.60 mmol) of sodium iodide. The reaction mixture was refluxed for 3.5 hours at which time it was diluted with 200 mL of a 1:1 mixture of water/hexane. The organic layer was washed with saturated sodium sulfite, dried (MgSO$_4$) and evaporated to provide 4.43 g of a pale yellow oil. The residue obtained was purified by filtration through 50 g of silica gel, eluting with hexane. Pure product fractions were combined to provide 4.29 g (91%) of title iodide as a colorless oil.

TLC Silica gel (hexanes) $R_f=0.56$.

IR (CCl$_4$) 2961, 2924, 1647, 1447, 1376, 1209, 1164 cm$^{-1}$.

$^1$H NMR (270 MHz, CDCl$_3$): δ 5.09 (m, 2H), 3.18 (t, 2H, J=7.0 Hz), 2.10 (m, 6H), 1.85 (quint, 2H, J=7.3 Hz), 1.69 (s, 6H), 1.62 (s, 3H) ppm.

MS (CI-NH$_3$, +ions) m/e 310 (M+NH$_4$), 292 (M).

B. (Z)-[1-(Ethoxymethylphosphinyl)-6,10-dimethyl-5,9-undecadienyl]phosphonic acid, diethyl ester To a stirred mixture of 123 mg (5.13 mmol) of sodium hydride in 10 mL of DMF at 0° C. under argon was added 1.32 g (5.13 mmol) of Example 1, Part A [(ethoxymethylphosphinyl)methyl]phosphonic acid, diethyl ester in 5 mL of DMF dropwise over 20 minutes. The mixture was stirred for 0.5 hours and was treated with 1.00 g (3.42 mmol) of Part A iodide in 3 mL of DMF. The reaction was stirred at 0° C. for 1 hour then at room temperature for 48 hours, at which time the reaction was diluted with ether and quenched with saturated NH$_4$Cl. The organic layer was washed with water, brine, dried (MgSO$_4$) and evaporated to provide 1.10 g of a pale yellow oil. Flash chromatography was performed on 100 g of silica gel eluted with 49.5:49.5:1 acetone/ethyl acetate/methanol (1 liter) followed by 45:45:10 acetone/ethyl acetate/methanol. Pure product fractions were combined and evaporated to provide 600 mg (43%) of title ester as a pale yellow oil, a mixture of diastereomers.

TLC Silica gel (95:5 dichloromethane/methanol) $R_f=0.30$.

IR (CCl$_4$) 2966, 2928, 1730, 1450, 1381, 1238, 1033 cm$^{-1}$.

$^1$H NMR (270 MHz, CDCl$_3$): δ 5.11 (m, 2H), 4.15 (m, 6H), 2.18 (m, 1H), 2.02 (m, 6H), 1.60-2.10 (m, 8H), 1.90 (m, 2H), 1.69 (s, 6H), 1.67, 1.66 (two d, 3H, J=13.9 Hz), 1.61 (s, 3H), 1.34 (t, 6H, J=7.3 Hz), 1.33 (t, 3H, J=6.7 Hz) ppm.

MS (CI-NH$_3$, +ions) m/e 440 (M+NH$_4$), 423 (M+H).

C. (Z)-[1-(Hydroxymethylphosphinyl)-6,10-dimethyl-5,9-undecadienyl]phosphonic acid, disodium salt To a stirred solution of 550 mg (1.30 mmol) of Part B ester in 20 mL of dichloromethane at room temperature under argon was added 429 μL (3.25 mmol) of 2,4,6-collidine followed by 858 μL (6.50 mmol) of bromotrimethylsilane. The reaction stirred for 48 hours, at which time the solvent was evaporated and the residue pumped for 2 hours. The remainder was treated with 4.30 mL (4.30 mmol) of 1M NaOH and lyophilized. The crude lyophilate was purified on SP207SS gel (2.5 cm diameter×27 cm height) eluted with water (100 mL) followed by a gradient created by the addition of 300 mL of 1:1 water/acetonitrile to a 300 mL reservoir of water. Approximately 10 mL fractions were collected. Product fractions were combined, evaporated to remove acetonitrile and lyophilized to provide 460 mg (93%) of title salt as a white amorphous lyophilate.

IR (KBr) 2965, 2928, 2859, 1632, 1163, 1082, 874 cm$^{-1}$.

$^1$H NMR (400 MHz, D$_2$O): δ 5.23 (t, 1H, J=7.1 Hz), 5.17 (m, 1H), 2.05 (m, 4H), 2.00 (m, 2H), 1.70 (m, 3H), 1.64 (s, 6H), 1.58 (s, 3H), 1.50 (m, 2H), 1.28 (d, 3H, J=13.9 Hz) ppm.

MS (FAB, +ions) m/e 427 (M+2Na−H), 405 (M+Na), 383 (M+H).

Anal. Calc'd for $C_{14}H_{26}P_2O_5Na_2 \cdot 1.1$ mol $H_2O$ C, 41.82; H, 7.07; P, 15.41 Found: C, 42.09; H, 6.90; P, 15.03.

EXAMPLE 10

(E,E,E,E)-[1-(Hydroxymethylphosphinyl)-4,8,12-trimethyl-1-(3,7,11-trimethyl-2,6,10-dodecatrienyl)-3,7,11-tridecatrienyl]phosphonic acid, disodium salt A. (E,E,E,E)-[1-(Ethoxymethylphosphinyl)-4,8,12-trimethyl-1-(3,7,11-trimethyl-2,6,10-dodecatrienyl)-3,7,11-tridecatrienyl]phosphonic acid To a stirred mixture of 380 mg (15.80 mmol) of NaH in 10 mL of DMF at 0° C. under argon was added dropwise 3.90 mL (15.80 mmol) of tetraethyl methylenediphosphonate. The reaction was stirred for 0.5 hours, then was treated with 1.50 g (5.26 mmol) of Example 3, Part A bromide. The reaction was stirred at 0° C. for 1 hour, at which time it was diluted with ether and quenched with NH$_4$Cl. The organic layer was washed with water, brine, dried (MgSO$_4$) and evaporated to provide 3.96 g of a pale yellow oil. Flash chromatography was performed on 200 g of silica gel eluted with ethyl acetate (500 mL) then with a 49.5:49.5:1 mixture of acetone/ethyl acetate/ methanol. Pure product fractions were combined and evaporated to provide 1.5 g (62%) of (E,E)-(4,8,12-trimethyl-3,7,11-tridecatrienylidene)bisphosphonic acid, tetraethyl ester as a pale yellow oil.

The title compound was obtained as a faster moving byproduct in the preparation of the above intermediate (21% yield, 500 mg).

TLC Silica gel (5: 95 Methanol/Dichloromethane) R$_f$=0.21.

IR (CCl$_4$) 2976, 2922, 2856, 1443, 1383, 1241, 1221, 1028, 961 cm$^{-1}$.

$^1$H NMR (270 MHz, CDCl$_3$): δ 5.40, 5.34 (two t, 2H total, J=7.04 Hz), 5.10–5.00 (m, 4H), 4.10 (m, 6H), 2.60 (m, 4H), 2.00 (m, 16H), 1.61 (d, 3H, J=14.07 Hz), 1.60 (s, 6H), 1.56 (s, 6H), 1.52 (s, 12H), 1.26 (t, 9H, J=7.04 Hz) ppm.

MS (CI-NH$_3$, +ions) m/e 667 (M+H), 665 (M+H−H$_2$), 597 (M+H−C$_5$H$_{10}$).

B. (E,E,E,E)-[1-(Hydroxymethylphosphinyl)-4,8,12-trimethyl-1-(3,7,11-trimethyl-2,6,10-dodecatrienyl)-3,7,11-tridecatrienyl]phosphonic acid, disodium salt To a stirred solution of 330 mg (0.495 mmol) of Part A diester in 10 mL of dichloromethane at room temperature under argon was added 132 μL (1.00 mmol) of 2,4,6-collidine followed by 264 μL (2.00 mmol) of bromotrimethylsilane. The reaction stirred at room temperature for 24 hours when the solvent was evaporated and the residue pumped under high vacuum for 1 hour. The remainder was dissolved in 7.2 mL (3.60 mmol) of 0.5M NaOH and lyophilized. The crude lyophilate was purified by MPLC on a column of CHP20P gel (2.5 cm diameter×20 cm height) eluted with water (fractions 1–17) followed by a gradient created by the gradual addition of 75:25 acetonitrile/water (400 mL) to a reservoir of 400 mL water. Approximately 15 mL fractions were collected. Pure product fractions were combined, evaporated to remove acetonitrile and lyophilized to provide 220 mg (70%) of title salt as a white lyophilate.

IR (KBr)3425, 2966, 2918, 2854, 1445, 1164, 1080, 1039 cm$^{-1}$.

$^1$H NMR (400 MHz, D$_2$O): δ 5.45 (m, 2H), 5.10–5.00 (two m, 4H), 2.50 (m, 4H), 2.10–1.80 (m, 17H), 1.58 (s, 12H), 1.52 (s, 6H), 1.50 (s, 6H), 1.26 (d, 3H, J=13.5 Hz) ppm.

MS (FAB, +ions) m/e 649 (M+Na), 627 (M+H), 609 (M+H−H$_2$O).

Anal. Calc'd for $C_{32}H_{54}P_2O_5Na_2 \cdot 0.60$ H$_2$O C, 60.29; H, 8.73; P, 9.72 Found: C, 60.33; H, 8.80; P, 9.97.

The following additional compounds suitable for use in the method of the invention for inhibiting cholesterol biosynthesis by inhibiting de novo squalene production may be prepared employing procedures set out hereinbefore in Examples 1 to 10.

(E,E)-[1-[hydroxy(methoxymethyl)phosphinyl]-6,10,14-trimethyl-5,9,13-pentadecatrienyl]phosphonic acid, salts thereof, esters thereof, mixed ester-salts thereof, or disodium or dipotassium salt;

(E)-[1-(hydroxymethylphosphinyl)-8,12-dimethyl-7,11-tridecadienyl]phosphonic acid, salts thereof, esters thereof, mixed ester-salts thereof, or trisodium or tripotassium salt;

[1-hydroxymethylphosphinyl)-4-[4-(2-methyl-1-propenyl)phenyl]butyl]phosphonic acid, salts thereof, esters thereof, mixed ester-salts thereof, or trisodium or tripotassium salt;

(E)-1-(hydroxymethylphosphinyl)-9,13-dimethyl-8,12-tetradecadienylphosphonic acid, salts thereof, esters thereof, mixed ester-salts thereof, or disodium or dipotassium salt;

(E)-[1-(hydroxymethylphosphinyl)-10,14-dimethyl-9,13-pentadecadienyl]phosphonic acid, salts thereof, esters thereof, mixed ester-salts thereof, or dipotassium or disodum salt;

(E)-1-[hydroxy(hydroxymethyl)phosphinyl]-6,10-dimethyl-5,9-undecadienylphosphonic acid, salts thereof, esters thereof, mixed ester-salts thereof, or trisodium or tripotassium salt;

(E)-1-[hydroxy(methoxymethyl)phosphinyl]-6,10-dimethyl-5,9-undecadienylphosphonic acid, salts thereof, esters thereof, mixed ester-salts thereof, or trisodium or tripotassium salt;

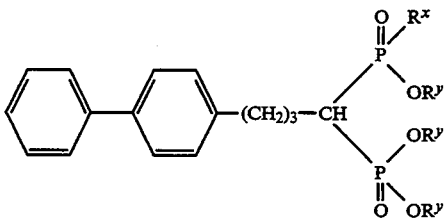

| R$^x$ | R$^y$ |
|---|---|
| CH$_3$ | H, Na or K |
| CH$_2$OH | H, Na or K |
| CH$_2$OCH$_3$ | H, Na or K |
| CH$_2$NH$_2$ | H, Na or K |

What is claimed is:

1. A method of inhibiting cholesterol biosynthesis by inhibiting de novo squalene production thereby inhibiting or treating hypercholesterolemia, which comprises administering to a patient in need of such treatment a therapeutically effective amount of a methylene phosphonoalkylphosphinate squalene synthetase inhibitor which includes at least one lipophilic group which is a group which contains at least 6 carbons, to inhibit de novo squalene production and thereby inhibit cholesterol biosynthesis.

2. The method as defined in claim 1 wherein the methylene phosphonoalkylphosphinate squalene synthetase inhibitor includes at least one lipophilic group which is a group which contains at least 6 carbons and is required for strong enzyme inhibitor binding and inhibition of the enzyme squalene synthetase or other enzymes in the cholesterol biosynthetic pathway.

3. The method as defined in claim 2 wherein the lipophilic group is optionally substituted alkyl, optionally substituted alkenyl or optionally substituted aryl.

4. A method of inhibiting cholesterol biosynthesis by inhibiting de novo squalene production thereby inhibiting or treating hypercholesterolemia, which comprises administering to a patient in need of such treatment a therapeutically effective amount of a methylene phosphonoalkylphosphinate squalene synthetase inhibitor having the structure

wherein $R_1$ is selected from hydrogen, substituted alkyl and unsubstituted alkyl, and A and B are independent substituent moieties, wherein A is a moiety selected from the group consisting of hydrogen; halogen; nitro; alkyl; heterocycle; aryl; heteroaryl; unsubstituted amino, and the amide thereof derived from a carboxylic acid of a substituent group; amino substituted with one substituent group and the amide thereof derived from a carboxylic acid of a substituent group; amino substituted independently with one alkyl group and one substituent group; hydroxy, and the ester thereof derived from a carboxylic acid of a substituent group; ether having a substituent group; thiol, and the thiol ester thereof derived from a carboxylic acid of a substituent group; thioether having a substituent group, and the sulfoxide and sulfone derivative thereof; —$SO_3H$, the pharmaceutically acceptable salts thereof, the ester thereof derived from an alcohol of a substituent group, the unsubstituted amide thereof and the amide thereof substituted with one or two alkyl groups; —$CO_2H$, the pharmaceutically acceptable salts thereof, the ester thereof derived from an alcohol of a substituent group, the unsubstituted amide thereof, and the amide thereof substituted with one or two alkyl groups; aldehyde; ketone having a substituent group; carbamate, unsubstituted or substituted with one or two alkyl groups; peptides having from about one to about 100 amino acid moieties; or the A and B moieties are covalently linked to form a ring having from 3 to 7 atoms with from 0 to 3 heteroatoms selected from the group consisting of nitrogen, sulfur, phosphorus and oxygen, the ring being unsubstituted or substituted with one or more of the above substituents of A; of the A and B moieties are replaced by an unsubstituted or substituted alkyl moiety attached to the geminal carbon by a double bond; and B is a moiety selected from hydrogen; halogen; unsubstituted and substituted lower alkyl; unsubstituted and substituted cycloalkyl having from 3 to 7 atoms in the ring; unsubstituted and substituted heterocycle having from 3 to 7 atoms in the ring; unsubstituted and substituted phenyl; hydroxy, and the ester thereof derived from a carboxylic acid of a lower alkyl group; thiol; unsubstituted amino, and the amide thereof derived from a carboxylic acid of a lower alkyl group; amino substituted with one lower alkyl group, and the amide thereof derived from a carboxylic acid of a lower alkyl group; amino substituted independently with two lower alkyl groups; —$CO_2H$, the pharmaceutically acceptable salts thereof, the ester thereof derived from an alcohol of a lower alkyl group, the unsubstituted amide thereof, and the amide thereof substituted with one or two lower alkyl groups, wherein at least one of A and B is a lipophilic group which is a group which contains at least 6 carbons and is required for strong enzyme inhibitor binding and inhibition of the enzyme squalene synthetase or other enzymes in the cholesterol biosynthetic pathway, to inhibit de novo squalene production and thereby inhibit cholesterol biosynthesis.

5. The method as defined in claim 3 wherein the lipophilic group is a straight or branched chain unsaturated alkyl containing 6 to 20 carbons.

6. The method as defined in claim 2 wherein alkyl includes cycloalkyl having from about 4 to about 10 carbons.

7. The method as defined in claim 5 wherein alkyl is straight chain monounsaturated alkyl.

8. The method as defined in claim 3 wherein alkyl is substituted with halogen, nitro, cyano, heterocycle, aryl, heteroaryl, unsubstituted amino, and the amide thereof derived from a carboxylic acid of an alkyl, heterocycle, aryl or heteroaryl group, amino substituted with one alkyl, heterocycle, aryl or heteroaryl group and the amide thereof derived from a carboxylic acid of an alkyl group, amino substituted independently with one alkyl group and one alkyl, heterocycle, aryl or heteroaryl group, hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide or sulfone derivative thereof, —$SO_3H$, a pharmaceutically acceptable salt thereof, the ester thereof derived from an alcohol of an alkyl group, the unsubstituted amide thereof, and the amide thereof substituted with one or two alkyl groups, —$CO_2H$, a pharmaceutically acceptable salt thereof, the ester thereof derived from an alcohol of an alkyl group, and the unsubstituted amide thereof, and the amide thereof substituted with one or two alkyl groups, $PO_3H_2$, a pharmaceutically acceptable salt thereof, the ester thereof derived from an alcohol of an alkyl group, the unsubstituted amide thereof, and the amide thereof substituted with one or two alkyl groups, —$(R^8)PO_2H$ (where $R^8$ is hydrogen or unsubstituted lower alkyl), a pharmaceutically acceptable salt thereof, the ester thereof derived from an alcohol of an alkyl group, the unsubstituted amide thereof, and the amide thereof substituted with one or two alkyl groups, aldehyde, ketone having an alkyl group, carbamate, unsubstituted or substituted with one or two alkyl groups, peptidyl, or a combination thereof.

9. The method as defined in claim 8 wherein the term "heterocycle" refers to chemically-stable non-aromatic rings having from about 5 to about 20 atoms, comprising at least one heteroatom selected from nitrogen, sulfur, phosphorus and oxygen.

10. The method as defined in claim 9 wherein heterocycle is piperidinyl or piperidinylidene.

11. The method as defined in claim 9 wherein the term "aryl" refers to a chemically-stable aromatic ring having from about 6 to about 20 carbon atoms.

12. The method as defined in claim 11 wherein aryl is phenyl or naphthyl.

13. The method as defined in claim 11 wherein aryl is unsubstituted or substituted with alkyl; halogen; nitro; cyano; heterocycle; aryl; heteroaryl, unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; amino substituted independently with one alkyl group and one alkyl, heterocycle, aryl or heteroaryl group; hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thioether having an alkyl, heterocycle, aryl or heteroaryl group, and the sulfoxide or sulfone derivative thereof; —$SO_3H$, a pharmaceutically acceptable salt thereof, the ester thereof derived from an alcohol of an alkyl group, the unsubstituted amide thereof, and the amide thereof substituted with one or two alkyl groups; —$CO_2H$, a pharmaceutically acceptable salt thereof, the ester thereof derived from an alcohol of an alkyl group, the unsubstituted amide thereof, and the amide thereof substituted with one or two alkyl groups; $PO_3H_2$, a pharmaceutically acceptable salt thereof, the ester thereof derived from an alcohol of an alkyl group, the unsubstituted amide thereof, and the amide thereof substituted with one or two alkyl groups; —$(R^8)PO_2H$ (where $R^8$ is hydrogen or unsubstituted lower alkyl), a pharmaceutically acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; peptidyl; or a combination thereof.

14. The method as defined in claim 3 wherein "heteroaryl" refers to a chemically-stable aromatic ring having from about 5 to about 20 atoms, comprising at least one heteroatom selected from nitrogen, sulfur, phosphorus and oxygen.

15. The method as defined in claim 14 wherein heteroaryl is pyridinyl.

16. The method as defined in claim 3 wherein the optional substituents on the $R_1$ alkyl is halogen, unsubstituted and substituted phenyl, unsubstituted and substituted pyridinyl, unsubstituted amino, amino substituted with one or two lower alkyl groups, hydroxy, carboxy, or a chemically-stable combination thereof.

17. The method as defined in claim 3 wherein the A moiety is (1) hydrogen;
(2) halogen;
(3) substituted and unsubstituted alkyl having the general structure:

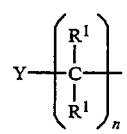

wherein
n is an integer from 1 to about 10;
each $R^1$ is independently selected to achieve chemically-stable moieties from the group consisting of hydrogen, halogen, lower alkyl, unsubstituted amino or the amido thereof derived from a carboxylic acid of a lower alkyl group, amino substituted with one lower alkyl group or the amide thereof derived from a carboxylic acid of a lower alkyl group, amino substituted independently with two lower alkyl groups, hydroxy or the ester thereof derived from a carboxylic acid of a lower alkyl group, —$CO_2H$ or a pharmaceutically acceptable salt thereof or the ester thereof derived from an alcohol of a lower alkyl group or the unsubstituted amide thereof or the amide thereof substituted with one or two lower alkyl groups, ether having a lower alkyl group, —$PO_3H_2$ or a pharmaceutically acceptable salt thereof, and nitro, or two $R^1$'s on the same carbon atom are =O or =$NR^9$ (where $R^9$ is lower alkyl or may be hydrogen when there is another nitrogen atom attached to the same carbon atom as the =$NR^9$ moiety), or two $R^1$'s on adjacent carbon atoms may be replaced by an additional bond between the carbon atoms; or an $R^1$ on the first carbon atom (from the right side of structure (2) hereinabove) and B (in structure (1)) may be replaced by an additional bond; and
Y is a substituent of alkyl as defined hereinbefore; for the sake of chemical stability, $R^1$ cannot be such that there is a halogen and an oxygen or sulfur or nitrogen singly bonded to the same carbon atom or such that two of an oxygen or sulfur or nitrogen are singly bonded to the same carbon atom;

(4) Cycloalkyl having from about 4 to about 10 carbon atoms;
(5) Heterocycle having 5 or 6 atoms in the ring;
(6) unsubstituted and substituted phenyl; naphthyl;
(7) Unsubstituted and substituted 5 and 6 membered ring heteroaryls having one or two heteroatoms;
(8) amine-containing moiety having the general structure:

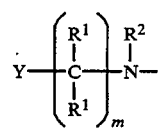

wherein
m is an integer from 0 to about 10;
$R^1$ and Y are as described hereinbefore, and
$R^2$ is hydrogen, lower alkyl or acyl derived from a carboxylic acid of a lower alkyl;

(9) oxygen-containing moiety having the general structure:

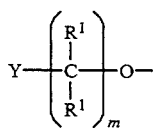

wherein m is an integer from 0 to about 10; and $R^1$ and Y are as described hereinbefore; and

(10) sulfur-containing moiety having the general structure:

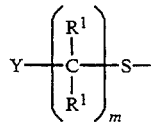

wherein m is an integer from 0 to about 10; and $R^1$ and Y are as described hereinbefore; or

(11) peptide-containing moiety having the general structure:

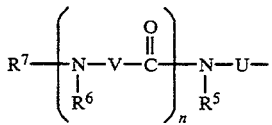

or

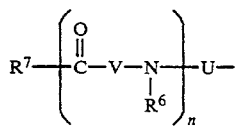

wherein n is an integer from 1 to about 100;

$R^5$, each $R^6$ and $R^7$ are independently hydrogen or lower alkyl;

U and each V are independently unsubstituted or substituted lower alkyl, or $R^5$ and U or each $R^6$ and V, together with the included nitrogen atom to which they are bound, may form a five- or six-membered ring which is unsubstituted or substituted; or U may be nil; or U and each V or rings in which they are incorporated are moieties found in naturally-occurring amino acid moieties, which are lysine, leucine, isoleucine, valine, phenylalanine, arginine, histidine, methionine, alanine, aspartic acid, threonine, proline, glycine, serine, tyrosine, tryptophan, glutamine or cysteine.

18. The method as defined in claim 14 wherein the A and B moieties are directly bonded via a C atom to the methylene phosphonoalkylphosphinate moiety.

19. The method as defined in claim 14 wherein the A moiety has an oxygen, sulfur, nitrogen, or halogen atom bonded to the phosphorous-substituted methylene carbon, then B is selected from hydrogen; unsubstituted or substituted lower alkyl, cycloalkyl, heterocycle wherein a carbon atom of the heterocycle is bonded to the geminal carbon atoms, or phenyl; —$CO_2H$, a pharmaceutically acceptable salt thereof, the ester thereof derived from an alcohol of a lower alkyl group, the unsubstituted amide thereof, and the amide thereof substituted with one or two lower alkyl groups.

20. The method as defined in claim 3 wherein B is selected from hydrogen, halogen, unsubstituted and substituted lower alkyl, unsubstituted and substituted phenyl, unsubstituted and substituted benzyl, hydroxy and the ester thereof derived from a carboxylic acid of a lower alkyl group, thiol, unsubstituted amino and the amide thereof derived from a carboxylic acid of a lower alkyl group, amino substituted with one lower alkyl group and the amide thereof derived from a carboxylic acid of a lower alkyl group, amino substituted independently with two lower alkyl groups, and —$CO_2H$, and the pharmaceutically acceptable salts thereof and the ester thereof derived from an alcohol of a lower alkyl group and the unsubstituted amide thereof or the amide thereof substituted with one or two lower alkyl groups.

21. The method as defined in claim 3 wherein the methylene phosphonoalkylphosphinate employed is (E,E)-[1-(hydroxymethylphosphinyl)-7,11,15-trimethyl-6,10,14-hexadecatrienyl]phosphonic acid, esters thereof, salts thereof, mixed ester-salts thereof, or its disodium salt; (E,E)-[1-(hydroxymethylphosphinyl)-6,10,14-trimethyl-5,9,13-pentadecatrienyl]phosphonic acid, including esters thereof, salts thereof, mixed ester-salts thereof, or its disodium salt; (E,E)-[1-(hydroxymethylphosphinyl)-4,8,12-trimethyl-3,7,11-tridecatrienyl]phosphonic acid, esters thereof, salts thereof, mixed ester-salts thereof, or its disodium salt; 1-(hydroxymethylphosphinyl)-10-methyl-9-undecenylphosphonic acid, esters thereof, salts thereof, mixed ester-salts thereof, or its tripotassium salt; (E)-[4,8-dimethyl-1-(hydroxymethylphosphinyl)-3,7-nonadienyl]phosphonic acid, esters thereof, salts thereof, mixed ester-salt thereof, or its trisodium salt; (E)-[1-(hydroxymethylphosphinyl)-6,10-dimethyl-5,9-undecadienylidene)-phosphonic acid, esters thereof, salts thereof, mixed ester-salt thereof, or its trisodium salt; (E)-[4-[4-(2,6-dimethyl-1,5-heptadienyl)phenyl]-1-(hydroxymethylphosphinyl)butyl]phosphonic acid, esters thereof, salts thereof, mixed ester-salts thereof, or its dipotassium salt; (E)-[1-(hydroxymethylphosphinyl)-7,11-dimethyl-6,10-dodecadienyl]phosphonic acid, esters thereof, salts thereof, mixed ester-salts thereof, or its dipotassium salt; (Z)-[1-(hydroxymethylphosphinyl)-6,10-dimethyl-5,9-undecadienyl]phosphonic acid, esters thereof, salts thereof, mixed ester-salts thereof, or its disodium salt; (E,E,E,E)-[1-(hydroxymethylphosphinyl)-4,8,12-trimethyl-1-(3,7,11-trimethyl-2,6,10-dodecatrienyl)-3,7,11-tridecatrienyl]phosphonic acid, esters thereof, salts thereof, mixed ester-salts thereof, or its disodium salt; (E)-1-[hydroxy(hydroxymethyl)phosphinyl]-6,10-dimethyl-5,9-undecadienylphosphonic acid, esters thereof, salts thereof, mixed ester-salts thereof, or its trisodium salt; (E)-1-[hydroxy(methoxymethyl)phosphinyl]-6,10-dimethyl-5,9-undecadienylphosphonic acid, esters thereof, salts thereof, mixed ester-salts thereof, or its trisodium salt.

22. The method as defined in claim 3 wherein the methylene phosphonoalkylphosphinate employed is (E,E)-[1-[hydroxy(methoxymethyl)phosphinyl]-6,10,14-trimethyl-5,9,13-pentadecatrienyl]phosphonic acid, salts thereof, esters thereof, mixed ester-salts thereof, or disodium or dipotassium salt;

(E)-[1-(hydroxymethylphosphinyl)-8,12-dimethyl-7,11-tridecadienyl]phosphonic acid, salts thereof, esters thereof, mixed ester-salts thereof, or trisodium or tripotassium salt;

[1-hydroxymethylphosphinyl)-4-(2-methyl-1-propenyl)phenyl]butyl]phosphonic acid, salts thereof, esters thereof, mixed ester-salts thereof, or trisodium or tripotassium salt;

(E)-[1-(Hydroxymethylphosphinyl)-10,14-dimethyl-8,12-tetradecadienylphosphonic acid, salts thereof, esters thereof, mixed ester-salts thereof, or disodium or dipotassium salt;

(E)-[1-(hydroxymethylphosphinyl)-10,14-dimethyl-9,13-pentadecadienyl]phosphonic acid, salts thereof, esters thereof, mixed ester-salts thereof, or dipotassium or disodum salt;

(E)-1-[hydroxy(hydroxymethyl)phosphinyl]-6,10-dimethyl-5,9-undecadienylphosphonic acid, salts thereof, esters thereof, mixed ester-salts thereof, or trisodium or tripotassium salt;

(E)-1-[hydroxy(methoxymethyl)phosphinyl]-6,10-dimethyl-5,9-undecadienylphosphonic acid, salts thereof, esters thereof, mixed ester-salts thereof, or trisodium or tripotassium salt;

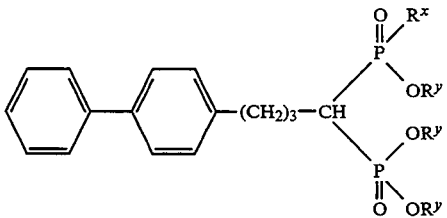

| $R^x$ | $R^y$ |
|---|---|
| $CH_3$ | H, Na or K |
| $CH_2OH$ | H, Na or K |
| $CH_2OCH_3$ | H, Na or K |
| $CH_2NH_2$ | H, Na or K |

* * * * *

UNITED STATES PATENT AND TRADEMARK OFFICE
CERTIFICATE OF CORRECTION

PATENT NO. : 5,428,028
DATED : June 27, 1995
INVENTOR(S) : Scott A. Biller et al It is certified that error appears in the above-identified patent and that said Letters Patent is hereby corrected as shown below:

In Claim 4, col. 37, line 61, after "substituents of A;" please change "of" to --or--.

In Claim 22, col. 43, line 3 should read
--[1-hydroxymethylphosphinyl)-4-[4-(2-methyl-1- --.

In Claim 22, col. 43, line 7, please change "-10,14-" to -- -9,13- --.

Signed and Sealed this

Fourteenth Day of November, 1995

BRUCE LEHMAN

Attest:

Attesting Officer

Commissioner of Patents and Trademarks